US005650270A

United States Patent [19]

Giese et al.

[11] Patent Number: 5,650,270
[45] Date of Patent: Jul. 22, 1997

[54] MOLECULAR ANALYTICAL RELEASE TAGS AND THEIR USE IN CHEMICAL ANALYSIS

[75] Inventors: Roger W. Giese, Quincy; Samy Abdel-Baky; Kariman Allam, both of Braintree, all of Mass.

[73] Assignee: Northeastern University, Boston, Mass.

[21] Appl. No.: 496,251

[22] Filed: Mar. 20, 1990

Related U.S. Application Data

[63] Continuation-in-part of Ser. No. 45,089, May 4, 1987, abandoned, which is a continuation of Ser. No. 344,394, Feb. 1, 1982, Pat. No. 4,709,016.

[51] Int. Cl.[6] .............. C12Q 1/68; G01N 33/53; G01N 31/00; G01N 33/561
[52] U.S. Cl. .............. 435/6; 435/7.2; 435/12; 435/175; 435/181; 435/183; 435/188; 435/280; 435/424; 436/2; 436/521; 436/536; 436/544; 436/547; 530/391.3; 530/391.5; 536/24.3; 536/23.1; 548/339.1; 548/542
[58] Field of Search .............. 548/542, 342, 548/339.1; 435/7, 188, 175, 181, 183, 12, 424, 280, 6, 7.2; 530/389, 390, 391; 536/27; 436/2, 536, 521, 547, 544

[56] References Cited

U.S. PATENT DOCUMENTS

| | | | |
|---|---|---|---|
| 3,317,559 | 5/1967 | Anderson | 548/542 |
| 4,112,219 | 9/1978 | Hlavka | 548/542 X |
| 4,171,311 | 10/1979 | Araps | 260/326.34 |
| 4,182,656 | 1/1980 | Ahnell et al. | 435/34 |
| 4,230,797 | 10/1980 | Boguslaski et al. | 435/7 |
| 4,231,999 | 11/1980 | Carlsson et al. | 424/1 |
| 4,261,893 | 4/1981 | Boguslaski et al. | 260/326 |
| 4,279,992 | 7/1981 | Boguslaski et al. | 435/7 |
| 4,288,243 | 9/1981 | Grove | 548/542 X |
| 4,318,981 | 3/1982 | Burd et al. | 435/7 |
| 4,331,590 | 5/1982 | Bocuslaski et al. | 260/112 B |
| 4,360,592 | 11/1982 | Weltman | 435/7 |
| 4,423,143 | 12/1983 | Rubenstein et al. | 435/7 |
| 4,487,838 | 12/1984 | Hynes et al. | 548/542 X |
| 4,650,750 | 3/1987 | Giese | 435/7 |
| 4,709,016 | 11/1987 | Giese | 530/389 |
| 4,730,050 | 3/1988 | Smith | 548/542 X |
| 4,794,189 | 12/1988 | Leone-Bay et al. | 548/542 |
| 5,045,303 | 9/1991 | Wilbur et al. | 548/542 X |
| 5,082,930 | 1/1992 | Nicolotti et al. | 548/542 X |

FOREIGN PATENT DOCUMENTS

| | | | |
|---|---|---|---|
| 0085554 | 8/1983 | European Pat. Off. | 548/542 |
| 2618511 | 11/1976 | Germany | 435/7 |
| 2901173 | 1/1979 | Germany | 435/7 |
| 2839836 | 3/1979 | Germany | 435/7 |
| 2839884 | 3/1979 | Germany | 435/7 |

OTHER PUBLICATIONS

Carlsson et al II, Biochem. J., 173, pp. 723–737, (1978), "Protein Thiolation and Reversible Protein–Protein Conjugation".

Gross, "Methods in Enzymology", vol. II, pp. 238–253 (1980).

Poole et al, Anal. Chem., 52(9), pp. 1002–1016, (1980), "Derivatization Techniques for the Electron–Capture Detector".

Giese III, abstract for C&EN 183rd ACS national meeting Mar. 28–Apr. 2 presentation—Release Tags: a New Class of Analytical Reagents (Feb. 15, 1982).

Giese IV, abstract for 14th annual symposium (Apr. 29–Apr. 30)—Advanced Analytical Concepts for the Clinical Laboratory.

Giese et al, Clinical Chemistry, 28(9), pp. 1844–1847, (1982), "Release Tags: a New Class of Analytical Reagents".

Giese V, Trends in Analytical Chemistry, 2(7), pp. 166–168, (1983), "Electrophoric release tags: ultrasensitive molecular labels providing multiplicity".

Theisen, Analytical Biochemistry, 152, pp. 211–214, (1986), "Sequential Detection of Antigens in Western Blots with Differently Colored Products".

Cohen, Analytical Chemistry, 54(8), p. 890, (1982), Editors' Column, "New Clinical Applications for Familiar Analytical Concepts".

BioRad Catalog, 1986, "Blotting Media".

Meeting Briefs from New York, C&EN, Apr. 28, 1986, "Reagents function as electrophoric labels".

Meriwether, Clinical Chemistry News, 8(6), (Jun. 1982), "Release Tags" column on Advanced Concepts at Oak Ridge Conference.

Parks et al, Cytometry 5(159), pp. 159–168, (1984), "Three–Color Immunofluorescence Analysis of Mouse B–Lymphocyte Subpopulations".

(List continued on next page.)

*Primary Examiner*—Floyd D. Higel
*Attorney, Agent, or Firm*—Weingarten, Schurgin, Gagnebin & Hayes LLP

[57] ABSTRACT

Analytical reagents designated "release tags", for labeling molecular species with a highly detectable signal group which can be released in the form of a volatile compound at a desired point in an analytical procedure. In one embodiment, the release tags have the formula $$(SgCo)_xL(Rx)_r$$

wherein each Sg is a signal group bearing one or more electronegative substituents, L is any of a wide variety of groups which when attached to a carbonyl group form a readily cleaved linkage, each COL moiety is a release group which upon scission releases signal group Sg in the form of a volatile compound, and each Rx is a reactivity group for attaching the release tag compound to a molecular species to be labeled. In a second embodiment, the release tags have the formula $$SgReRx$$

wherein Sg and Rx are defined as above and Re is a release group which is an olefin, α-hydroxy ketone or vicinal diol. Conjugates of the release tag compounds and assay methods employing them are also disclosed.

11 Claims, 3 Drawing Sheets

OTHER PUBLICATIONS

Boorsma et al, J. of Microscopy, 143(2), pp. 197–203, (1986), "Simultaneous immunoenzyme double labelling using two different enzymes linked directly to monoclonal antibodies or with biotin–avidine".

Newallis et al, J. Org. Chem., 30, pp. 3834–3837, (1965), "Fluoro Ketones. III. Preparation and Thermal Decomposition of Fluoroacetone Hemiketal Esters".

Yates et al I, J. Org. Chem., 34, p. 256?, (1969), "The Thermal Decomposition of β–Hydroxy Ketones".

Yates, et al II J. Org. Chem., 36, pp. 3379–3382, (1971), "The Thermal Decomposition of β–Hydroxy Esters".

Arnold et al, J. Am. Chem. Soc., 81, pp. 6443–6445, (1959), "The Pyrolysis of β–Hydroxyolefins".

Smith et al, Nature, 321, pp. 674–679, (1986), "Fluorescence detection in automated DNA sequence analysis".

Goralski et al, NEN Product News, 3(4), pp. 2–3, (Jun. 1984), "Repetitive Screening of the Drosophila Genomic Library".

Haase et al, Science, 227, pp. 189–192, (Jan. 1985), "Detection of Two Viral Genomes in Single Cells by Double–Label Hybridizatoin in Situ and Color Microradioautography".

Peterson et al, Science, 227, pp. 1361–1364, (Mar. 1985), "Multiple Stable Isotopes Used to Trace the Flow of Organic Matter in Estuarine Food Webs".

Sidki et al, Therapeutic Drug Monitoring, 7, pp. 101–107, (1985), "Dual–Label Fluoroimmunoassay for Simultaneous Determination of Primidone and Phenobarbital".

Jacobs et al, J. Biol. Chem., 250, pp. 3629–3636 * (1986).

Anthony G.M. Barrett, et al., "Phenol Oxidation and Biosynthesis. Part 27. Reactions of Relevance to the Formation of Erysodienone in vitro." in Journal of The Chemical Society, Perkin Transactions I, vol. 3, pp. 662–668, 1979.

MOLECULAR ANALYTICAL RELEASE TAGS AND THEIR USE IN CHEMICAL ANALYSIS

CROSS-REFERENCE TO RELATED APPLICATIONS

This is a continuation-in-part of application Ser. No. 07/045,089 filed May 4, 1987, now abandoned, which is a continuation of application Ser. No. 06/344,394 filed Feb. 1, 1982, now U.S. Pat. No. 4,709,016. A related application is Ser. No. 06/591,262 filed Mar. 19, 1984, which was a division of application Ser. No. 06/344,394, and has now issued as U.S. Pat. No. 4,650,750. Another related application is application Ser. No. 06/710,318 filed Mar. 11, 1985, now U.S. Pat. No. 5,360,819 which is a continuation in part of application Ser. No. 06/344,394. The text of application Ser. No. 06/344,394 is hereby incorporated herein by reference.

STATEMENT OF GOVERNMENT SUPPORT

This invention was made with government support under Contract N00019-82-K-0811 awarded by the Defense Advanced Research Projects Agency. The Government has certain rights in this invention.

FIELD OF THE INVENTION

This invention pertains to analytical chemical reagents, and more particularly, to cleavable reagents for labeling molecular species in analytical procedures and subsequently releasing and detecting signal-producing molecules.

BACKGROUND OF THE INVENTION

Chemical signal groups are widely used in chemical analysis to label substances of interest such as analytes, internal standards, comparison substances, and specific binding partners for analytes, so that such materials can be followed, detected, or determined in analytical procedures.

Examples of signal groups include radioactive atoms, fluorescent and luminescent molecules, metal-containing compounds, electron-absorbing groups; enzymes, and light-absorbing compounds.

Presently-used chemical signal groups suffer from a variety of shortcomings. Radioactive atoms in many cases have short half lives, present safety and disposal problems, and cause compounds containing them to be physically unstable and/or chemically labile. In addition, some radioactive materials do not provide high sensitivity, either because they do not produce a high level of radioactivity or because beta particles produced in the decomposition of the radioactive atoms are quenched by the medium to a substantial extent before they can be detected. Also, a variety of closely related radioactive tracers which might be employed and measured simultaneously in a single system are not available. Nonradioactive signal groups suffer from the deficiencies that the signal can be dependent on the environment of the label, which necessitates careful matching of the matrices of samples and standards if accurate data are to be obtained, that the effective signal can be reduced by any dilution of the sample during the analytical procedure, and that possibilities for using multiple labels simultaneously in a single analytical system are limited because of mutual interferences.

Traditional labels are typically retained on the labeled molecular species, and the presence or amount of the labeled material is determined by measuring the signal from the label while still attached to the remainder of the molecule, and often, in the presence of other constituents of the analytical system. As labeled species frequently contain a variety of moieties which can interfere with the measurement of the desired signal, and in addition, the labeled species cannot always be easily brought into a medium which is optimum for the measurement of the signal from the label, this can constitute a serious limitation on the utility of labels generally in a particular system, or on the use of particular labels which an investigator might wish to use.

An example of such traditional label usage is the common practice of labeling molecules with electron-absorbing groups. The molecules are inherently volatile or are rendered volatile by the labeling operation. They can then be determined in the gas phase by gas chromatography with electron capture detection (GC-ECD) or by GC with detection by electron capture negative ion mass spectrometry (GC-ECNI-MS).

The literature contains a few examples of indirect determinations of analytes by determination of a molecular species produced by decomposition of the analyte or chemical cleavage of a derivative of the analyte. An example of the former is the determination of trichloroacetic acid by decarboxylation and measurement of the resulting chloroform. See Buchet, et al., Arch. Mal. Prof. Med. Tray., 35, 395–402 (1974); and Senft, J. Chromatogr., 337, 126–130 (1985). An example of the latter is the analysis for $T_4$ toxin by formation of the labeled derivative N-(N-pentafluoro-benzoyl-Met-Gly)-$T_4$ followed by cyanogen bromide cleavage to produce N-pentafluorobenzoyl homoserine lactone. See U.S. Pat. Nos. 4,650,750 and 4,709,016 by R. W. Giese.

Another example of an indirect determination of an analyte is shown in U.S. Pat. No. 4,629,689 of Diamond. This reference discloses analytical schemes in which at the conclusion of a selective binding assay an enzyme is present in a concentration and/or activity which is related to the amount of analyte present in the sample, and this enzyme is measured by measuring the amount of a readily detectable signal group released from a cleavable conjugate of the signal group and another molecular species by the action of the enzyme. As an example, the enzyme β-galactosidase was determined by measuring the amount of o-nitrophenol released by the enzyme-catalyzed cleavage of o-nitrophenyl-β-D-galactopyranoside.

It is very desirable to have labeling reagents which do not suffer from many or most of the above-described disadvantages of traditional reagents, and, most importantly, permit multiple species to be labeled and determined in a single sample. Such reagents are the subject of the present application.

SUMMARY OF THE INVENTION

A new class of labeling reagents has recently been conceived, and is undergoing continued development. These reagents, called "release tags," are basically three-part molecules which can be illustrated by the generic formula Sg-Re-Rx in which Sg represents a "signal" group which may be determined readily by an analytical detection device, Rx represents a "reactivity" group containing a functional group which reacts with a substance to be labeled, thereby attaching the release tag, and Re represents a "release" group at which cleavage can occur at an appropriate time and under appropriate conditions to release the signal group Sg in a form suitable for determination.

The three-part nature of release tags permits a wide variety of such materials to be prepared by varying each of the segments. Particularly where the signal groups Sg contain electrophilic atoms and thereby are electrophoric (electron-absorbing in the gas phase), large numbers of closely-related release tag compounds can be prepared by selecting various combinations of the electrophilic atoms and substituent groups for incorporation into Sg. The reactivity groups Rx can also be varied widely to provide release tags capable of bonding specifically and selectively to particular substances to be labeled, or to particular classes of such substances, as desired. Finally, the release groups Re can be varied widely to provide release tags which can be cleaved under particular desired conditions to release signal group-containing molecules for analytical detection or determination.

The totality of these features is thus seen to provide the potential for a vast multiplicity of release tags, each of which can ultimately release a signal group different from those of other release tags. In principle, each of a series of many substances can be separately labeled with a different release tag. Subsequently the labeled substances can be brought together and employed as a combined, analytical reagent. Since the "signal" molecules can be released and determined simultaneously, a large number of analytes in the sample can be measured simultaneously. Release tags are thus seen to be extremely powerful analytical tools.

Examples of analytical undertakings in which release tags will be of great value are the human genome project, infectious disease testing such as AIDS, and genetic screening. The need for multiple labels for such purposes has been expressed. See e.g., Landegren, U., Kaiser, R., Caskey, C. T. and Hood, L., "DNA Diagnostics-Molecular Techniques and Automation", Science 242, 229–237, 1988; Rotman, D., "Sequencing the Entire Human Genome", Industrial Chemist, Dec. 18–26, 1987; Giese, R. W., "Electrophoric Release Tags: Ultrasensitive Molecular Labels Providing Multiplicity", Trends in Anal. Chem. 2, 166–168, 1983.

The present application relates to two classes of release tag compounds. The first of these classes includes release tag compounds which are cleaved to release signal group-containing molecules by hydrolysis followed by decarboxylation. The second class includes release tag compounds which release the signal group by oxidation followed by decarboxylation. Included in both classes are release tag compounds which may also release the signal group thermally, hydrothermally, or by a related mechanism.

In one of its aspects, the present invention relates to release tag compounds for labeling substances for analytical purposes, these compounds being represented by the formula

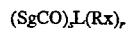  (I).

In formula (I), each Sg is a signal group, each CO is a carbonyl group to which an Sg is bonded, each Rx is a reactivity group, L is a linking group to which each SgCO group and each Rx group are bonded, each COL portion is a release group which is cleavable to release an Sg-containing compound, s is an integer of at least one, and r is an integer of at least one.

Further, each Sg is a C-linked organic moiety containing from 1 to 20 carbon atoms, the carbon atom of Sg which is bonded to the carbonyl carbon adjacent to linking group L being denominated as the α-position, and comprises a radical selected from the group consisting of substituted alkyl, substituted keto-alkyl, substituted alkenyl, and substituted alkynyl radicals. When Sg comprises a substituted alkyl, substituted keto-alkyl, or substituted alkenyl radical, it bears at least two electronegative substituents; and when Sg comprises a substituted alkynyl radical, it bears at least one electronegative substituent, these electronegative substituents being selected from the group consisting of halogens, cyano, dihalomethyl, and trihalomethyl.

When Sg is keto-alkyl, alkenyl, or alkynyl, it comprises at least one moiety selected from the group consisting of β-E-alkynyl, α-E-α-alkynyl, β-E-α-keto (provided that the carbonyl carbon adjacent to linking group L is connected to a nitrogen or oxygen atom of L), α-E-alkenyl, and α-E-α-alkenyl, wherein E is an electronegative substituent selected from the group consisting of halogens, cyano, dihalomethyl, and trihalomethyl. When Sg is β-E-alkynyl, it can bear only one electronegative substituent, this being clear from the structure of this group as shown in Table I. Sg groups which comprise the other moieties listed here will contain at least two electronegative substituents.

When Sg is alkyl, the α-carbon atom bears at least two of said electronegative substituents but no more than one fluorine atom.

Further, each Sg has properties such that upon release from the release tag compound, it forms an electrophoric compound which is sufficiently volatile for determination in the gas phase.

L comprises one of the following groups: oxy, carbonyloxy, amino, hydrazino, aminooxy, carbonylamino, carbonylhydrazino, carbonylaminooxy, N-pyrrolidino, N-1, 4-diaminopiperazino, O-linked tris-(hydroxymethyl)-methylamino; an O-linked monosaccharide residue derived from a monosaccharide containing only C, H, and C; an O-linked monosaccharide residue derived from a monosaccharide possessing at least one amino, hydrazino, or hydrazido group; and a polymer residue derived from a polymer possessing a plurality of functionalities selected from the group consisting of hydroxyl, carboxyl, primary and secondary amines, amides, and hydrazides.

Each Rx is a C-linked or $SO_2$-linked organic moiety comprising 1–20 carbon atoms and at least one reactive functional group compatible with each SgCOL portion of the release tag compound and capable of covalently reacting the release tag compound via Rx with a labelable substance.

When Sg is $CHCl_2$, $CCl_3$, or $CBr_3$ and L is an amino moiety, Rx comprises a moiety selected from the group consisting of carbonylhydrazino, sulfonyl, phenylene, pyridinyl, pyrimidinyl, and vinyl. When L is an amino moiety —NH— directly linked to an alkyl moiety of the Rx group, the amino nitrogen may be directly linked to a maximum of one —$CH_2$— unit. When L comprises a polymer residue derived from a polyamide, the polyamide is a synthetic polyamide.

The invention also relates to molecular conjugates in which at least one of the above-described release tag compounds of formula (I) is covalently bound to at least one labelable substance having a reactive site capable of reacting with the reactivity group of the release tag compound, and to chemical assays which employ release tag compounds or conjugates of such compounds with labelable substances.

In a second aspect, the invention relates to additional release tag compounds for labeling substances for analytical purposes, these compounds being represented by the formula

  (II).

In formula (II), Sg is a signal group, Re is a release group to which Sg is covalently linked and which is cleavable to result in Sg release, and Rx is a reactivity group covalently linked to the Re group.

The group Sg of formula II is an organic moiety comprising at least one electronegative substituent and having properties such that upon release from the release tag compound, it forms an electrophoric compound which is sufficiently volatile for determination in the gas phase.

The group Re of formula II comprises a functionality selected from the group of cleavable linkages consisting of vicinal diols, α-hydroxy ketones, and olefins.

Finally, the group Rx of formula II is an organic moiety comprising 1–20 carbon atoms and at least one reactive functional group compatible with the release group Re and capable of covalently reacting the release tag compound via Rx with a labelable substance.

The invention further relates to molecular conjugates in which at least one of the above-described release tag compounds of formula (II) is covalently bound to at least one labelable substance having a reactive site capable of reacting with the reactivity group of the release tag compound, and to chemical assays which employ the above-described release tag compounds or conjugates of such compounds with labelable substances.

DESCRIPTION OF THE DRAWING

The invention will be more completely understood from a consideration of the following detailed description taken in conjunction with the drawing, in which.

DETAILED DESCRIPTION OF THE INVENTION

Figure 1A:
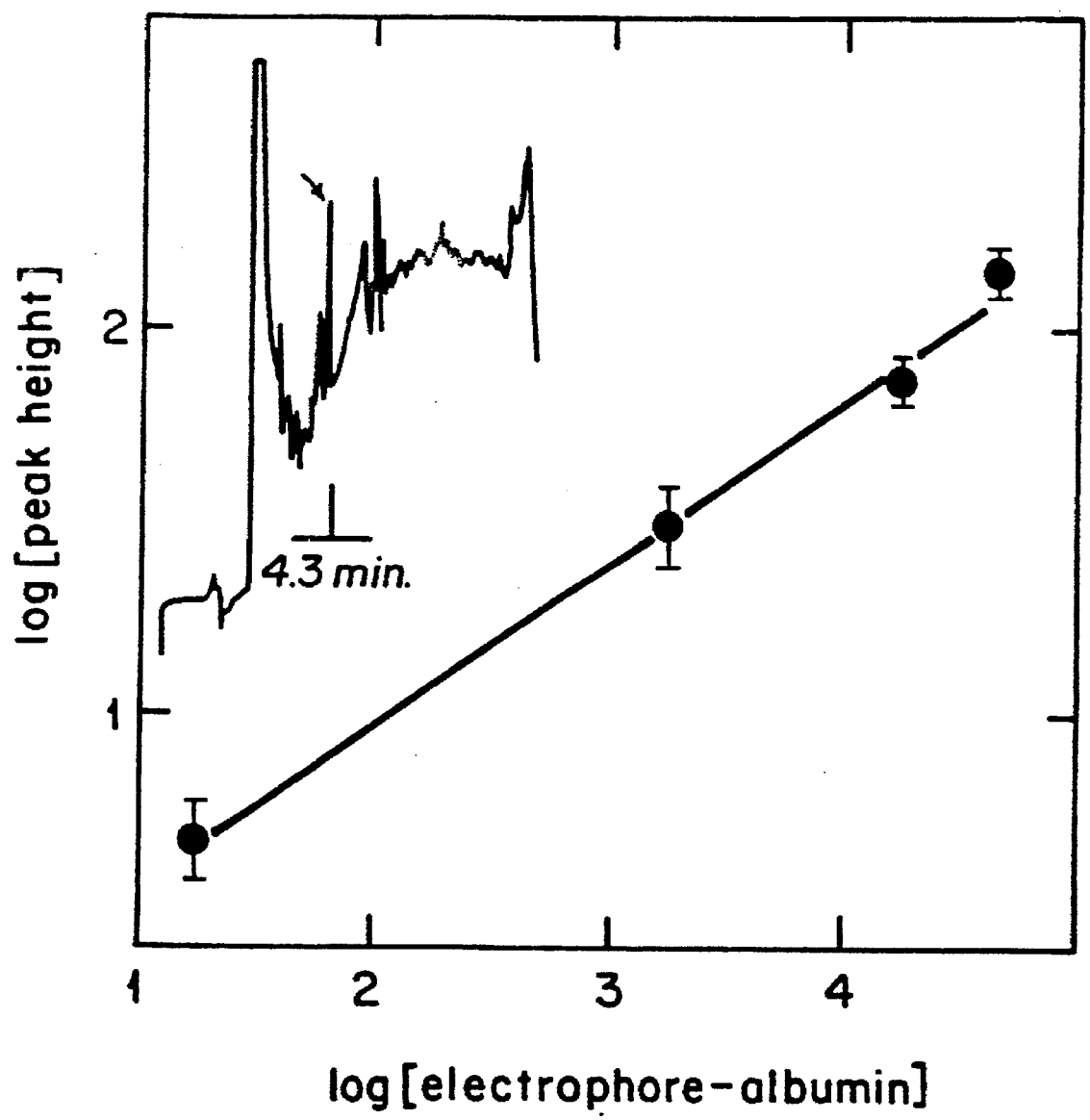
FIG. 1A is a calibration curve showing the signal provided by chloroform released from $2.4 \times 10^{-16}$ to $6 \times 10^{-13}$ moles of the release tag conjugate $CCl_3CO$-AB-BSA.

As indicated above, the first class of release tag compounds of the present application, those which hydrolyze and decarboxylate to release a volatile signal molecule, can be represented by the general formula:

$$(SgCO)_sL(Rx)_r \quad (I)$$

wherein s and r are each integers of at least one, but may be more than one.

Within Formula I are four subclasses of release tag compounds:
a) SgCOLRx corresponding to the case where both s and r are one;
b) $(SgCO)L(Rx)_r$ corresponding to the case where s is one and r is greater than one;
c) $(SgCO)_sLRx$ corresponding to the case where s is greater than one and r is one;
d) $(SgCO)_sL(Rx)_r$ corresponding to the case where both s and r are greater than one.

It is thus seen that the release tag compounds can range from moderately simple molecules to quite complex materials bearing several signal, release, and reactivity groups.

The signal groups Sg contain from 1 to 20 carbon atoms and are linked to carbonyl groups via a carbon atom of Sg. The carbon atom of Sg which is adjacent to the carbonyl group is designated as the α carbon, that adjacent to the α carbon atom is designated the β carbon, and that adjacent to the S carbon atom is designated as a γ carbon atom, in accordance with normal usage.

Each Sg group is a substituted alkyl, substituted keto-alkyl, substituted alkenyl, or substituted alkynyl group. Where Sg is substituted alkyl, substituted keto-alkyl, or substituted alkenyl, it bears at least two electronegative substituents selected from the group consisting of halogens, cyano, dihalomethyl, and trihalomethyl. When Sg is substituted alkynyl, it bears at least one such electronegative substituent, or at least two such electronegative substituents if its structure permits. Preferably, each Sg group contains three or more such electronegative substituents, providing its structure permits this degree of substitution, for good sensitivity as a signal group, this being especially true when Sg is alkyl.

More particularly, when Sg is a keto-alkyl, alkenyl, or alkynyl group, it is β-E-alkynyl, α-E-α-alkynyl, β-E-α-keto, α-E-alkenyl or α-E-α-alkenyl group. In the above-listed groups, E stands for an electronegative substituent selected from the group consisting of halogens, cyano, dihalomethyl, and trihalomethyl. Where the signal group Sg is a β-E-alkynyl group, it necessarily bears only a single E substituent. Further, where signal group Sg is a β-E-α-keto group, the carbonyl carbon atom adjacent to linking group L is connected to a nitrogen or oxygen atom of L.

The chemical structures of the above-identified keto-alkyl, alkenyl, and alkynyl groups are shown below in Table I.

TABLE I

Structural Formulae of Preferred Keto-Alkyl, Alkenyl, and Alkynyl Groups for Sg

| Name | Structure |
| --- | --- |
| β-E-alkynyl | E—C≡C—<br>  β   α |
| α-E-α-alkynyl | E<br>\|<br>—C≡C—C—<br>         \|<br>         α |
| β-E-α-keto | O<br>\|  \|\|<br>E—C—C—²<br>\|   α<br>β |
| α-E-alkenyl | E<br>\|<br>\C=C—<br>/   α |
| α-E-α-alkenyl | E<br>\|<br>\C=C—C—<br>/      α |

Footnotes for Table I:
[1]E is halogen, cyano, dihalomethyl, or trihalomethyl.
[2]In this case, the carbonyl carbon atom to which the α carbon is attached is in turn connected to an oxygen or nitrogen atom of L.

The Sg groups in Table I were selected for their ease of forming sensitive, electrophoric products SgH from corresponding parent compounds $SgCO_2H$, $(SgCO)_sL(Rx)_r$, or substances labeled by the release tag compounds $(SgCO)_sL(Rx)_r$.

When signal group Sg of formula I is alkyl, the R-carbon atom bears at least two of these electrolegative substituents but no more than one fluorine atom. Two electronegative substituents are required to be on the R-carbon for alkyl Sg, in order to facilitate the subsequent formation of SgH, and to make SgH sensitive as an electrophoric species. The presence of two or three fluorine atoms on the R-carbon does not adequately achieve these properties.

A further criterion for signal group Sg of formula I is that upon release from the release tag compound, the released fragment containing the Sg group ultimately forms an electrophoric compound which is sufficiently volatile for determination in the gas phase. This is to facilitate detection and quantitation of the ultimately formed electrophoric compounds by techniques such as gas chromatography and mass spectrometry.

The most preferred signal groups Sg comprise an alkyl or keto-alkyl moiety. Signal groups comprising an alkenyl moiety constitute a second choice, while signal groups comprising alkynyl moieties are somewhat less preferred.

The preferred electronegative substituents for inclusion in signal group Sg are the cyano group and the halogens fluorine, chlorine, and bromine. A signal- group will typically include at least two electronegative substituents, which may be the same or different, and where there are two or more electronegative substituents in Sg, two of these may be located on a single carbon atom or on different carbon atoms of the signal group. As the sensitivity of Sg as a signal group increases up to a point, with the number of electronegative substituents incorporated therein, preferred signal groups contain at preferred signal groups are those which contain Particularly two or three carbon atoms and three to five halogen atoms selected from the group consisting of chlorine and bromine.

Linking group L of formula I comprises one of the following groups: oxy, carbonyloxy, amino, hydrazino, aminooxy, carbonylamino, carbonylhydrazino, carbonylaminooxy, N-pyrrolidino, N-1,4-diaminopiperazino, an O-linked tris(hydroxymethyl) methylamino; an O-linked monosaccharide residue derived from a monosaccharide containing only C, H, and O; an O-linked monosaccharide residue derived from a monosaccharide possessing at least one amino, hydrazino, or hydrazido group; a polymer residue derived from a polymer possessing a plurality of functionalities selected from the group consisting of hydroxyl, carboxyl, primary and secondary amines, amides, and hydrazides. Structures of these linking groups are shown in Table II below.

TABLE II

Structural Formulae[1] of Linking Groups L

| Description | Structure |
|---|---|
| oxy | —O— |
| carbonyloxy | —C(=O)—O— |
| amino | —N(—)— |
| hydrazino | —N(—)—N(—)— |
| aminooxy | —N(—)—O— |
| carbonylamino | —C(=O)—N(—)— |
| carbonylhydrazino | —C(=O)—N(—)—N(—)— |
| carbonylaminooxy | —C(=O)—N(—)—O— |
| N-pyrrolidino | —N(pyrrolidine ring) |
| N-1,4-diaminopiperazino | H—N(H)—N(piperazine)N—N(H)—H |
| O-linked tris-(hydroxymethyl)-methylamino | —O—CH$_2$, —O—CH$_2$—C(—N(H)—)—O—CH$_2$ |
| O-linked monosaccharide residue derived from a monosaccharide containing only C, H, and O | |
| O-linked monosaccharide residue derived from a monosaccharide possessing at least one amino, hydrazino, or hydrazido group | |
| polymer residue derived from a polymer possessing a plurality of functionalities | |

TABLE II-continued

Structural Formulae[1] of Linking Groups L

| Description | Structure |
|---|---|
| selected from the group consisting of hydroxyl, carboxyl, primary and secondary amines, amides, and hydrazides | |

Footnote for Table II:
[1]The partial structural formulae illustrated in this table are employed in formula I in the direction shown.

Where the group L of formula I is —NH— linked to an alkyl moiety of the Rx group, the amino nitrogen may be directly linked to a maximum of one —$CH_2$— group in series with the —NH— group, as otherwise the amide may not be readily cleaved.

Where the group L of formula I is amino, hydrazino, aminooxy, carbonylamino, carbonylhydrazino, or carbonylaminooxy, the nitrogen atom(s) may bear hydrogen, an alk-$G_1$ substituent, or an alk-$G_2$ substituent, wherein "alk" is an alkyl moiety of 1 to 4 carbon atoms, and $G_1$ and $G_2$ are defined as follows. $G_1$ stands for hydrogen (—H); carboxymethyl (—$CO_2CH_3$); carbonylamino (—$CONH_2$); acetyl (—$COCH_3$); acetoxy (—$OCOCH_3$); methoxy (—$OCH_3$); sulfate (—$OSO_3H$); formamido (—NHCOH); acetamido (—$NHCOCH_3$); thiomethyl (—$SCH_3$); sulfonate (—$SO_3H$); sulfoxymethyl (—$SOCH_3$); sulfonyl methyl (—$SO_2CH_3$); or sulfonamide (—$SO_2NH_2$). The substituent $G_2$ may be hydroxy (—OH); carboxy (—$CO_2H$); or an imidazole (—$C_3H_3N_2$) group.

Where linking group L of formula I is N-pyrrolidino or N-1,4-diaminopiperizino, the ring may contain up to two substituents -$R^d$ where -$R^d$ is hydrogen, alk-$G_1$, -alk-$G_2$, -$G_1$, or -$G_2$, these groups having been defined above.

These substituents were selected for their ability to facilitate the formation of SgH. They were also selected for their ability to increase the water solubility of the release tag and its conjugates.

Where linking group L of formula I is tris-(hydroxymethyl)methylamino, each oxygen atom may and generally will bear an SgCO- group.

Where linking group L of formula I is an O-linked monosaccharide residue derived from a monosaccharide containing only C, H, and O, the monosaccharide from which L is derived may be any of a wide variety of monosaccharides, including various trioses, tetroses, pentoses, and hexoses. As is well known, these materials can generally exist in closed-ring and open-chain forms, both of which are in principle useful in the present invention. Where the monosaccharide exists as a closed ring, it is linked to SgCO- groups and to -Rx groups through its hydroxyl functionalities. Where the monosaccharide exists in the open-chain form, it is linked to SgCO- groups through its hydroxyl moieties, but may be linked to the -Rx portion of the release tag compound through its hydroxyl moieties, and also by means of derivatives of an aldehyde or ketone functionality which may be present in the open-chain form of the molecule. Some examples of monosaccharides which are useful in the present invention are materials such as erythrose, arabinose, xylose, ribose, lyxose, glucose, galactose, mannose, gulose, idose, talose, altrose, allose, fructose, sorbose, and tagatose.

Where linking group L of formula I is an O-linked monosaccharide residue derived from a monosaccharide possessing at least one amino, hydrazino, or hydrazido group, the starting monosaccharide may again be a triose, tetrose, pentose, hexose, which contains one or more nitrogen atoms in the form of an amino, hydrazino, or hydrazido group. As before, both closed-ring and open-chain nitrogen-containing monosaccharides function in the invention. In the release tag compounds of the invention including linking groups L derived from nitrogen-containing monosaccharides, the hydroxyl groups of the monosaccharide carry SgCO- groups while the amino, hydrazino, or hydrazido reactive functionality is employed in the connection to the reactivity group -Rx. Examples of a number of nitrogen-containing monosaccharides useful in the invention are shown in Table III below.

TABLE III

Examples of Monosaccharides containing Amino, Hydrazino, or Hydrazido Groups

| Name | Structure |
|---|---|
| glucosamine | [closed ring form] ⇌ [open chain CHO, $NH_2$, HO, OH, OH, $CH_2OH$] ⇌ [closed ring form with $NH_2$] |
| 2,3,4,5,6-pentahydroxy-hexylamine | $HOCH_2(CHOH)_4CH_2NH_2$ |
| 2,3,4,5,6-pentahydroxy- | $HOCH_2(CHOH)_4CH_2NHNH_2$ |

TABLE III-continued

Examples of Monosaccharides containing Amino, Hydrazino, or Hydrazido Groups

| Name | Structure |
|---|---|
| hexylhydrazine | |
| 2,3,4,5,6-pentahydroxy-hexylcarbohydrazide | $HOCH_2(CHOH)_4CH_2NHNHCONHNH_2$ |
| 2,3,4,5,6-pentahydroxy-caproylhydrazide | $HOCH_2(CHOH)_5CONHNH_2$ |
| 1-amino-[1H]-gluconic acid | $HO_2C(CHOH)_4CH_2NH_2$ |
| 1-hydrazino-[1H]-gluconic acid | $HO_2C(CHOH)_4CH_2NHNH_2$ |

Where linking group L of formula I is a polymer residue, it is derived from a naturally-occurring (except for polyamides) or synthetic polymer having multiple, generally repeating, reactive functionalities such as hydroxyl, carboxyl, primary and secondary amino, amido, and hydrazido groups. Preferred polymers are water soluble. Examples of biopolymers and derivatives thereof which can be employed in the invention are: polysaccharides and polysaccharide derivatives such as dextran, dextran hydrazide, chitosan, and glycol chitosan; natural polynucleotide derivatives such as sonicated calf thymus DNA which has been transaminated on its cytosine residues with carbohydrazide, an alkyldihydrazide, or an alkyl diamine; and synthetic polycytosine DNA oligomers which have similarly been transaminated.

Some examples of synthetic polymers and derivatives thereof which can be employed in the invention are: poly(aspartic acid), poly(aspartic acid) hydrazide, poly(glutamic acid) hydrazide, polyserine, polyglycine, poly(cytidylic acid), poly(asparagine), poly(glutamine), poly(acrylic acid), poly(acrylic acid) hydrazide, and poly(acrylamide) hydrazide. In the release tag compounds of the invention, some of the reactive functional groups on the polymer carry SgCO groups, while at least one of the reactive functional groups is connected to reactivity group Rx. By thus having a relatively large number of signal groups in the release tag compound, the sensitivity of assays employing the release tag is significantly increased. Analytical reagents such as specific binding proteins (e.g. antibodies) or specific binding polynucleotides (DNA probes) can be labeled with polymeric release tags, thereby to attach a large number of releasable signal groups. Tiny amounts of these polymeric release tag-labeled analytical reagents can then be detected at appropriate points in analytical schemes, providing highly sensitive assays. Structures of the above-listed polymers and polymer derivatives are shown in Table IV below.

TABLE IV

Examples of Polymers Containing Multiple Hydroxyl, Carboxyl, Amido, Amino, or Hydrazido Groups

| Name | Structure |
|---|---|
| dextran[1] | (dextran structure) |
| dextran hydrazide[2, 9] | (structure with $CH_2CONHNH_2$, or $-CONHNHCO \sim CONHNH_2$) |
| chitosan | (chitosan structure) |

TABLE IV-continued

Examples of Polymers Containing Multiple Hydroxyl, Carboxyl, Amido, Amino, or Hydrazido Groups

| Name | Structure |
|---|---|
| a glycol chitosan[3,9] | (structure shown) |
| a carbohydrazide derivative of a polynucleotide[4,9] | (structure shown) |
| polyaspartic acid | (structure shown) |
| polyaspartic acid hydrazide[5,9] | (structure shown) |
| polyglutamic acid hydrazide[6,9] | (structure shown) |
| polyserine | (structure shown) |
| polyglycine | (structure shown) |

TABLE IV-continued

Examples of Polymers Containing Multiple Hydroxyl, Carboxyl, Amido, Amino, or Hydrazido Groups

| Name | Structure |
|---|---|
| a carbohydrazide derivative of polycytidylic acid[4,9] | [structure with cytosine ring bearing NHNHCNHNH$_2$ group, ribose with O—CH$_2$, OH, and phosphate O=P—O$^\ominus$]$_n$ |
| polyasparagine | H$_2$N—CH(CH$_2$CONH$_2$)—C(=O)—[NH—CH(CH$_2$CONH$_2$)—C(=O)]$_n$—NH—CH(CH$_2$CONH$_2$)—C(=O)—OH |
| polyglutamine | H$_2$N—CH((CH$_2$)$_2$CONH$_2$)—C(=O)—[NH—CH((CH$_2$)$_2$CONH$_2$)—C(=O)]$_n$—NH—CH((CH$_2$)$_2$CONH$_2$)—C(=O)—OH |
| polyacrylic acid | —CH$_2$—CH(CO$_2$H)—CH$_2$—CH(CO$_2$H)— |
| polyacrylic acid hydrazide[7,9] | —CH$_2$—CH(CO—NHNH$_2$)—CH$_2$—CH(CO—OH)— |
| polyacrylamide hydrazide[8,9] | —CH$_2$—CH(CO—NH$_2$)—CH$_2$—CH(CO—NHNH$_2$)— |

Footnotes for Table IV:

[1] Although the structure of dextran shows α-1,6 linkages, there are occasional α-1,2, α-1,3, and α-1,4 linkages depending on the species. See Stryer, "Biochemistry", W. H. Freeman & Co., N.Y., p. 342 (1988).

[2] Preparation according to Wilchek and Boyer, Meth. Enz., 138E, 429–442 (1987), by reacting dextran with chloroacetic acid to form randomly-located —O—CH$_2$CO$_2$H groups, followed by reaction of these with hydrazine, or with a dihydrazide in the presence of a water-soluble carbodiimide. Dextran hydrazides may also be prepared by reacting dextran with hydrazine or a dihydrazide in the presence of borohydride or cyanoborohydride.

[3] The hydroxyethyl groups may be located on various —OH functionalities of the chitosan. Chitosan is reacted with ethylene oxide or 2-bromoethanol to form glycolchitosan.

[4] In the example shown, the cytosine residues of a DNA have been reacted with carbohydrazide in the presence of sodium bisulfite according to Reines and Schulman, Meth, Enz., LIX, 146–156 (1979), resulting in transamination. Alkyldiamines can be used similarly, as can alkyldihydrazides.

[5] Preparation according to Wilchek and Boyer, note [2] above, by reaction of poly-β-benzyl-L- aspartate with hydrazine. Alternatively, polyaspartate can be reacted with hydrazine or a dihydrazide in the presence of a water soluble carbodiimide.

[6] Prepared like polyaspartic acid hydrazide but with polyglutamate as the starting material.

[7] Prepared by reacting polyacrylic acid with hydrazine.

[8] Commercially available.

[9] Derivatives of polymers having multiple derivatizable functional groups are not necessarily fully derivatized, and generally contain some underivatized functional groups.

Carboxylic acid functionalities of the polymer or derivatized polymer can be reacted under appropriate conditions with reagents such as hydrazine, a dikydrazide such as carbohydrazide or adipic dihydrazide, or an aminoalkyl hydrazide, etc., to yield various hydrazide-containing derivatives. Similarly, such carboxylic functionalities can be reacted with various alkyl diamines or alkyl triamines to yield amino derivatives. Such reactions generally employ a reactive ester of the carboxylic acid as the starting material or as an intermediate in the reaction. Hydrazide-containing compounds can be further derivatized by reaction with succinic anhydride, followed by coupling to carbohydrazide or to some other dihydrazide, in the presence of a water soluble carbodiimide, to yield another form of hydrazide derivative.

The most preferred linking groups L are the oxy, carbonyloxy, carbonylamino, carbonylhydrazino, O-linked tris-(hydroxymethyl)methylamino, O-linked glucosamino, and O-linked polyserine. Where the reactive functional group of reactivity group Rx is a nucleophile, the most preferred linking groups L are the carbonylamino and carbonylhydrazino groups. A second preferred set of linking groups L includes the amino, hydrazino, N-pyrrolidino, and N-substituted polyaspartate hydrazide groups.

The reactivity group Rx of Formula I may be represented further by the general formula L'QRf, where L' is a linking functionality which connects the L and Q groups, Rf is the reactive functional group of reactivity group Rx, and Q is a spacer moiety bound to Rf and separating this reactive functional group from the rest of the molecule. Thus (SgCO)$_s$L(Rx)$_r$ is (SgCO)$_s$L(L'QRf)$_r$.

The linking functionality L' is a chemical bond or a multiatom moiety having a molecular weight of less than approximately 400 atomic mass units. It is bonded to linking group L via a carbon atom or an SO$_2$ group of L' and is compatible with each SgCOL portion and each reactive functional group Rf of the release tag compound.

The linking functionalities comprising the L' group are shown in TABLE V below.

TABLE V

Structural Formulae of Linking Functionalities L'

| Description | Structure |
|---|---|
| chemical bond | — |
| carbonyl | 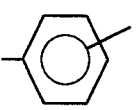 |
| carbonylamino | 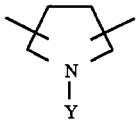 |
| carbonylhydrazino | 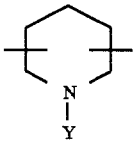 |
| sulfonyl | —SO$_2$— |
| alkyl of 1–10 carbons | —Alk— |
| phenylene | 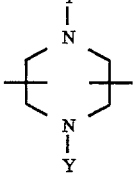 |
| C-pyrrolidinyl | 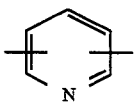 |

TABLE V-continued

Structural Formulae of Linking Functionalities L'

| Description | Structure |
|---|---|
| C-piperidinyl | 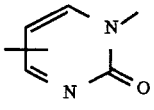 |
| C-piperazinyl | |
| pyridinyl | |
| 2-oxo-pyrimidinyl | |
| vinyl | 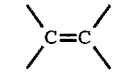 |

The partial formulae shown in this table are employed in Formula I in the direction shown.

Where L' is alkyl, phenylene, C-pyrrolidinyl, C-piperidinyl, C-piperazinyl, pyridinyl, or oxo-pyrimidinyl, it may be substituted with up to two substituent groups R$^d$ as defined above with respect to linking groups L. Where L' is vinyl, it may contain two substituent groups R$^e$ as defined above. The groups designated as Y residing on nitrogen atoms in the pyrrolidinyl, piperidinyl, or piperazinyl structures may be hydrogen, an alkyl group of one to three carbons, or —COCH$_3$.

Linking functionality L' is joined to spacer group Q by a chemical bond or, in the case where L' is alkyl, phenylene, pyrrolidinyl, piperidinyl, piperazinyl, pyridinyl, oxo-pyrimidinyl, or vinyl, L' may also be linked to Q by a further linker such as an oxy, amino, hydrazino, aminocarbonyl, hydrazinocarbonyl, carbonylamino, carbonylhydrazino, or carbonyl group. Where such linker contains a nitrogen atom, this may in turn bear a further substituent of hydrogen, or alkyl or acyl groups of one to three carbon atoms. Where the linkage between groups L' and Q involves a nitrogen or oxygen atom being bonded to group L', this may not be connected to a carbon atom of L' which already bears another hetero atom.

Linking functionality L' is preferably a chemical bond, a phenylene group, or an alkyl group of one to ten carbons.

The spacer moiety Q contains one to 15 carbon atoms and is linked to linking group L via a carbon atom of Q either directly when L' is a chemical bond, or indirectly through L' when L' is a multiatom moiety. Furthermore, Q is a function of the linkage between L and Q and the linkage between Q and reactive functional group Rf such that widen each of these linkages involves a hetero atom bonded to Q, such hetero atoms are separated from each other by at least two carbon atoms of Q. Preferably, when the linkage between L and Q as well as the linkage between Q and the reactive functional group Rf each involves a hetero atom bonded to Q, Q includes a 2-carbon aliphatic chain or a phenylene group.

The reactive functional group Rf of reactivity group Rx is an acylating, alkylating, electrophilic, or nucleophilic functionality.

When linking functionality L' is a multiatom moiety, L' includes one of the following groups: carbonyl, carbonylamino, carbonylhydrazino, sulfonyl, an alkyl group of one to ten carbon atoms, phenylene, C-pyrrolidinyl, C-piperidinyl, C-piperazinyl, pyridinyl, pyrimidinyl, and vinyl.

When linking group L is an oxy, carbonyloxy, aminooxy, or carbonylaminooxy moiety, L' is a chemical bend or a multiatom moiety including one of the following groups: alkyl of one to ten carbon atoms, phenylene, C-pyrrolidinyl, C-piperidinyl, C-piperazinyl, pyridinyl, 2-oxo-pyrimidinyl and vinyl.

When linking group L is oxy or carbonyloxy, reactive functional group Rf is an acylating, alkylating, or electrophilic functionality.

When linking group L is O-linked tris-(hydroxymethyl) methylamino, an O-linked monosaccharide residue, or an O-linked polymer residue, L' is a chemical bond or a multiatom moiety including one of the following groups: carbonyl, carbonylamino, carbonylhydrazino, sulfonyl, alkyl of one to 10 carbon atoms, phenylene, C-pyrrolidinyl, C-piperidinyl, C-piperazinyl, pyridinyl, pyrimidinyl, and vinyl; and Rf is an acylating, alkylating, or electrophilic functionality.

When linking group L is amino, hydrazino, carbonylamino, carbonylhydrazino, N-pyrrolidino, or N-(1,4-diaminopiperazino), L' is a chemical bond or a multiatom moiety including one of the following groups: carbonyl, carbonylamino, carbonylhydrazino, sulfonyl, alkyl of one to ten carbons, phenylene, C-pyrrolidinyl, C-piperidinyl, C-piperazinyl, pyridinyl, pyrimidinyl, and vinyl; and Rf is an acylating, alkylating, electrophilic, or nucleophilic functionality.

Where L is —NH— it may be directly linked in turn to a maximum of one —$CH_2$— group, alkyl chains $(CH_2)_n$ where n is >1 being disfavored since amides having the structure —$CONH(CH_2)_n$— may not be readily cleaved.

Where the reactive functional group Rf is an acylating functionality, it may be a carbodiimide-activated carboxyl group, an α-hydroxysuccinimide ester, a 1-hydroxybenzotriazole ester, a nitrophenyl ester, an acyl azide, an acyl halide such as the chloride, an acyl imidazole, an acyl pyridine such as that resulting from use of dimethylaminopyridine, an anhydride, an alkoxyanhydride, a thioester, an imidoester, a thioimidoester, phenyl isothiocyanate, an oxycarbonylimidazole, or an N-carboxyanhydride. General structures of these reactive functional groups are shown in Table VI.

TABLE VI

Structural Formulae for Acylating Rf Groups

| Description | Structure |
|---|---|
| carbodiimide-activated carboxyl | —C(=O)—O-carbodiimide[1] |
| N-hydroxysuccinimide ester | —C(=O)—N(succinimide) |
| 1-hydroxybenzotriazole ester | —O—N(benzotriazole) |
| nitrophenyl ester | —C(=O)—O—C6H4—$NO_2$ |
| acyl azide | —C(=O)—$N_3$ |
| acyl halide | —C(=O)—X |
| acyl imidazole | —C(=O)—N(imidazole) |
| acyl pyridine | —C(=O)—N⊕(pyridine)—N< |
| anhydride | —C(=O)—O—C(=O)— |
| alkoxyanhydride[2] | —C(=O)—O—C(=O)—O—R |
| thioester[2] | —C(=O)—S—R |
| imidoester[2] | —C(=NH2⊕)—O—R |
| thioimidoester[2] | —C(=NH2⊕)—S—R |
| phenylisothiocyanate | C6H5—N=C=S |
| oxycarbonylimidazole | —O—C(=O)—N(imidazole) |

TABLE VI-continued

Structural Formulae for Acylating Rf Groups

| Description | Structure |
|---|---|
| N-carboxyanhydride | (structure shown) |

Footnotes for Table VI:

[1] Exemplary carbodiimides are dicyclohexylcarbodiimide, 1-ethyl-3-(3-dimethylaminopropyl)carbodiimide, and 1-cyclohexyl-3-(2-morpholinyl)-4-ethyl carbodiimide-metho-p-toluene sulfonate. Generally, the release tag compound is prepared with one or more carboxyl groups as initial reactive functional groups, and these groups are caused to react with the carbodiimide to form the carbodiimide-activated carboxyl illustrated, which in turn reacts with the substance to be labeled.

[2] R is alkyl

[3] It will be recognized that many of the groups listed in Table VII may bear one or more substituents.

Where the reactive functional group Rf is an alkylating functionality, it may be an α-haloketo, a primary alkyl bromide or iodide, an epoxide, an alkoxypyridinium salt, an imine, a sulfonyloxyalkyl group, or a vinyl sulfone. Structures of these groups are shown below in Table VII.

TABLE VII

Structural Formulae for Alkylating Rf Groups

| Description | Structure |
|---|---|
| α-haloketo[1] | $-C(=O)-CH_2X$ |
| primary alkyl bromide or iodide | $-CH_2-(Br\ or\ I)$ |
| epoxide | $-CH-CH_2$ (with O bridge) |
| alkoxypyridinium salt[2] | $-O-$ pyridinium $N^{\oplus}-R$ |
| imine | $-CH-CH_2$ (with NH bridge) |
| sulfonyloxyalkyl (tresyloxyalkyl illustrated) | $-CH_2-O-SO_2-CH_2CF_3$ |
| vinyl sulfone | $-SO_2CH=CH_2$ |

Footnotes for Table VII:
[1] X is halogen
[2] R is alkyl

Where the reactive functional group Rf is an electrophilic functionality, it may be a nitrophenyl nitrene, an aldehyde, a maleimide, a disulfide, an α-diketone, a β-diketone, or a sulfonyl halide. Structures of these groups are shown in Table VIII below.

TABLE VIII

Structural Formulae for Electrophilic Rf Groups

| Description | Structure |
|---|---|
| nitrophenyl nitrene precursor[1] | nitrophenyl azide ($N_3$, $NO_2$) |
| aldehyde | $-C(=O)H$ |
| maleimide | (maleimide structure) |
| disulfide | $-S-S-$(2-pyridyl) |
| α-diketone[2] | $-C(=O)-C(=O)-R$ |
| β-diketone[2] | $-C(=O)-CH-C(=O)-R$ |
| sulfonyl chloride | $-SO_2Cl$ |

Footnotes for Table VIII:
[1] The nitrene ($-N$:) is generated by loss of $N_2$ from the azide.
[2] R is H or alkyl Where the reactive functional group Rf is a nucleophilic functionality, it may be a hydrazine, hydrazide, thiol, 1° or 2° amine, or oxyamine. Structures of these groups are shown in Table IX below.

TABLE IX

Structural Formulae for Nucleophilic Rf Groups

| Description | Structure |
|---|---|
| hydrazine | $-NHNH_2$ |
| hydrazide | $-C(=O)-NHNH_2$ |
| thiol | $-SH$ |
| amine | $-NH_2$ or $-NHR$ |
| oxyamine | $-O-NH_2$ |

The most preferred reactive functional groups Rf are the carbodiimide-activated carboxyls, N-hydroxysuccinimide esters, 1-hydroxybenzotriazole esters, acyl azides, and phenylisothiocyanates. A second set of preferred reactive functional groups are the nitrophenyl nitrenes, while a third set of reactive functional groups includes amines and hydrazides.

Preferred release tag compounds of Formula I are those which incorporate the several preferred Sg, L, L', and Rf groups as discussed above. The subsets of release tag compounds derivable by permutations of the preferred subsets of the Sg, L, L', and Rf groups are all preferred materials. Thus, preferred release tag compounds are those constructed employing the Sg, L, L', and Rf groups listed in Table X below, in which the numbers 1, 2, and 3 refer to first, second, and third choice subsets of the respective groups, and 1' refers to a most preferred but narrow subset of linking group L to be employed when reactive functional group Rf is a nucleophile.

TABLE X

Selected Combinations of Preferred Sg, L, L' and Rf Groups

| | Sg | L | L' | Rf |
|---|---|---|---|---|
| 1 | 1 | 1 | 1 | 1 |
| 2 | 1 | 1 | 1 | 2 |
| 3 | 1 | 1' | 1 | 3 |
| 4 | 1 | 2 | 1 | 1 |
| 5 | 1 | 2 | 1 | 2 |
| 6 | 1 | 2 | 1 | 3 |
| 7 | 2 | 1 | 1 | 1 |
| 8 | 2 | 1 | 1 | 2 |
| 9 | 2 | 1' | 1 | 3 |
| 10 | 2 | 2 | 1 | 1 |
| 11 | 2 | 2 | 1 | 2 |
| 12 | 2 | 2 | 1 | 3 |
| 13 | 3 | 1 | 1 | 1 |
| 14 | 3 | 1 | 1 | 2 |
| 15 | 3 | 1' | 1 | 3 |
| 16 | 3 | 2 | 1 | 1 |
| 17 | 3 | 2 | 1 | 2 |
| 18 | 3 | 2 | 1 | 3 |

Turning now to the set of release tag compounds having the general formula $$SgReRx \qquad (II),$$

signal group Sg is a C-linked organic moiety containing from one to twenty carbon atoms, the carbon atom of Sg which is bonded to the release group Re being denominated as the α-position since cleavage at Re generates initially an SgCO-moiety. Sg includes a substituted alkyl, substituted keto-alkyl, substituted alkenyl, or substituted alkynyl group, these groups bearing at least one halogen, cyano, dihalomethyl, or trihalomethyl electronegative substituent, though where the structure of Sg permits, higher numbers of electronegative substituents are preferred, as indicated below.

Further, when signal group Sg is keto-alkyl, alkenyl, or alkynyl, it is a β-E-alkynyl, α-E-α-alkynyl, β-E-α-keto, α-E-alkenyl, or α-E-α-alkenyl group, where E is a halogen, cyano, dihalomethyl, or trihalomethyl group.

Furthermore, when signal group Sg is alkyl, the α-carbon atom bears at least two of these E moieties but no more than one fluorine atom.

The electronegative substituents of signal group Sg are preferably selected from the group consisting of cyano and halogens.

The electronegative substituents of signal group Sg may be different, may be halogens, and may be located on different carbon atoms of the signal group.

Signal group Sg of formula II most preferably bears at least two electronegative substituents, and most preferably bears at least three electronegative substituents, which are preferably halogens of at least two different varieties. Two of these electronegative substituents are preferably located on different carbon atoms, although two of these electronegative substituents may be located on a single carbon atom of the Sg group. Particularly preferred signal groups are those which contain two or three carbon atoms and three to five halogen atoms selected from the group consisting of chlorine and bromine.

As indicated above, the release group Re of the release tag compounds represented by Formula II is a vicinal diol, an α-hydroxy ketone, or an olefin. Representative structures of these release groups are presented in Table XI below.

TABLE XI

Release Groups of Release Tag Compounds of Formula II

| Description | Structure |
|---|---|
| vicinal diol | OH OH<br>|  |<br>—C—C—<br>|  |<br>    H |
| α-hydroxy ketone | O  OH<br>|| |<br>—C—C—<br>    | |
| | OH O<br>|  ||<br>—C—C—<br>|<br>H |
| olefin | 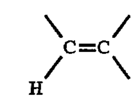 |

The reactivity group Rx of the release tags of Formula II is represented by the formula QRf, wherein Rf is a reactive functional group which is compatible with the release group portion of the release tag compound and also capable of forming a covalent bond with a labelable substance, and Q is a chemical bond or a C-linked spacer moiety bound to the Rf group and including from one to fifteen carbon atoms. Further, Q is a function of the Rf group and the linkage between the release group Re and Q such that when the release group is an oxirane or an α-hydroxy ketone and is linked via its α-carbon atom to the Q group, and the reactive functional group Rf is linked to Q via a hetero atom, Q comprises at least one carbon atom.

The reactive functional group Rf of Formula II is an acylating, alkylating, electrophilic, or nucleophilic functionality, except that where release group Re is a vicinal diol or an α-hydroxy ketone, reactivity group Rf may not be a sulfonyl halide.

Where reactive functional group Rf of release tag Formula II is an acylating functionality, it is a carbodiimide-activated carboxyl, an α-hydroxysuccinimide ester, a 1-hydroxybenzotriazole ester, a nitrophenyl ester, an acyl imidazole, an acyl pyridine, a thioester, or an imidoester. Structures of these reactive functional groups are shown in Table VI.

Where the reactive functional group Rf of release tag Formula II is an alkylating functionality, it is an α-haloketo group, a primary alkyl bromide or iodide, an epoxide, an alkoxypyridinium salt, or an imine. Structures of these reactive functional groups are shown in Table VII.

Where the reactive functional group Rf of release tag Formula II is an electrophilic functionality, it is a nitrophenyl nitrene precursor, an aldehyde, a maleimide, a disulfide, an α-diketone, a β-diketone, or a sulfonyl halide. Structures of these reactive functional groups are shown in Table VIII.

Where the reactive functional group Rf of release tag Formula II is a nucleophilic functionality, it is a hydrazine, a hydrazide, a thiol, an amine, or an oxyamine. Structures of these reactive functional groups are shown above in Table IX.

In the release tag compounds of formula II, the most preferred signal groups Sg are substituted alkyl or keto-alkyl groups, a second choice being substituted alkenyl groups. The most preferred release groups Re are α-hydroxyketones, with vicinal diols being a second choice. The most preferred reactive functional groups Rf are the carbodiimide-activated carboxyls and α-hydroxysuccinimide esters, with the second choice groups being nitrophenyl nitrene precursors, hydrazides, and amines. Preferred release tag compounds of Formula II are those which include various permutations of the first and second choices of the Sg, Re, and Rf groups discussed above. Accordingly, preferred release tag compounds of Formula II are indicated in Table XII below, where the number 1 represents the most preferred options for the particular portion of the release tag compounds, and number 2 represents the second choices for these functionalities.

TABLE XII

Preferred Release Tag Compounds of Formula II

| | Sg | Re | Rf |
|---|---|---|---|
| 4 | 1 | 1 | 1 |
| 5 | 1 | 1 | 2 |
| 6 | 1 | 2 | 1 |
| 7 | 1 | 2 | 2 |
| 8 | 2 | 1 | 1 |
| 9 | 2 | 1 | 2 |
| 10 | 2 | 2 | 1 |
| 11 | 2 | 2 | 2 |

Other preferred release tag compounds of Formula II are those in which the release group Re includes a vicinal diol or an α-hydroxy ketone, and the reactive functional group Rf includes a carbodiimide-activated carboxyl group or an N-hydroxysuccinimide ester acylating functionality.

The release tag compounds of the invention are useful for labeling any substance, provided that the substance to be labeled possesses at least one functional group capable of reacting with the reactive functional group Rf of reactivity group Rx of the release tag compound to be employed. To put it another way, the release tag compounds of the invention make it possible to label a vast number of substances which either possess or can be modified to possess a reactive functional group, by providing one or more release tags with reactive functional groups capable of reaction with the reactive functional groups of the substance to be labeled, and causing these materials to react to form a covalent linkage.

Among the many sorts of substances which aloe capable in principle of being labeled by the release tag compounds of the invention are materials one wishes to analyze for, generally referred to as analytes, and analogs of such analytes; materials which constitute primary or secondary binding partners for such analytes or analyte analogs; and various substrates for enzymes which are used as labels on analyte analogs and on primary and secondary binding partners for various analytes.

Representative examples of analytes which may be labeled by the release tag compounds of the invention are materials such as a) proteins: for example, protein hormones such as insulin, thyroid stimulating hormone (TSH), growth hormone (GH), follicle stimulating hormone (FSH), and luteinizing hormone (LH); enzymes such as creatine kinase and lactate dehydrogenase (LDH); tumor antigens such as carcinoembryonic antigen (CEA); antibodies such as anti human immunodeficiency virus (A'HIV), A'hepatitis, IgE, and $IgG_1$; receptors such as progesterone receptor and estrogen receptor; and transport proteins such as α-lipoprotein and transferrin;

b) peptides: for example, hormones such as angiotensin II, glucagon, and adrenocorticotrophic hormone (ACTH);

c) amino acids such as triiodothyronine ($T_3$), tetraiodothyronine or thyroxin ($T_4$) and γ-aminobutyric acid;

d) polynucleotides: for example, gene fragments and genes such as the AIDS gene and the sickle Hb gene; and RNA such as mRNA, tRNA, rRNA;

e) nucleotides such as adenosine monophosghate (AMP);

f) nucleosides such as $N^2$-(dG-8-yl)-2-aminofluorene;

g) nucleobases such as 5-methylcytosine;

h) lipids: for example, steroids such as cortisol, estradiol, and aldosterone; and prostaglandins such as $PGE_2$;

i) carbohydrates such as blood group antigens;

j) drugs such as digoxin and theophylline;

k) cells: for example, lymphocytes such as B lymphocytes and T lymphocytes;

l) viruses such as the hepatitis, HIV-I, and HIV-II;

m) vitamins such as Vitamin A, Vitamin D, Vitamin E, Vitamin $B_{12}$, and folic acid;

n) coenzymes such as NAD;

o) bioactive amines such as epinephrine end dopamine;

p) aflatoxins such as aflatoxin $B_1$ and aflatoxin $G_1$;

q) polyaromatic hydrocarbons such as benzo[a]pyrene, and 7,12-dimethylbenz[a]anthracene;

r) pesticides such as dieldrin and aldrin.

A primary binding partner for an analyte is a substance that forms a specific noncovalent complex with the analyte. For many types of analytes, corresponding antibodies may be obtained as primary bonding partners. Such analytes are classified into two broad classes based on their sizes—antigens (which are large) and haptens (which are small). Sometimes an antibody is the analyte of interest, in which case the corresponding antigen or hapten is used as the specific binding partner.

Other classes of primary binding partners also exist. A certain nucleic acid (DNA or RNA) or fragment thereof may be an analyte, in which case the complementary nucleic acid (DNA or RNA), generally termed a "DNA probe" when it comprises DNA, is the primary binding partner. An enzyme can be a binding partner for an inhibitor as an analyte, or vice versa. Similarly, lectins bind sugars, avidin and its analogs (e.g., streptavidin and succinylavidin) bind biotin, and receptors bind messenger substances such as hormones and neurotransmitters. As before, either one of the substances in each of these pairs is a primary binding partner for the other.

A secondary binding partner is a substance that binds to a primary binding partner even after the primary binding partner has become bound to its analyte. For example, if antibody $Ab_1$ binds analyte An, forming a complex $Ab_1$•An, and a second antibody $Ab_2$ is available which binds in turn to the prior complex onto the $Ab_1$ part, forming $Ab_2$•$Ab_1$•An, then $Ab_2$ is a secondary binding partner for the analyte. The binding of $Ab_2$ onto $Ab_1$ is thus "piggyback" in nature. The site on $Ab_1$ that is recognized by $Ab_2$ may either be an inherent part of $Ab_1$, or a hapten or antigen recognized by $Ab_2$ that has been conjugated to $Ab_1$.

Since protein A and protein G bind to antibodies at regions remote from the antibody binding site, they are often used as secondary binding partners in immunoassays.

Biotin commonly is attached to an antibody for an analyte so that avidin (or an avidin analog), which specifically binds to biotin, can function as a secondary binding partner relative to the analyte against which the antibody was developed. If a conjugate of an antibody $Ab_1$ and avidin (i.e., Av-$Ab_1$) binds to an analyte An forming the complex Av-$Ab_1$•An and this complex in turn can bind to biotin forming biotin•Av-$Ab_1$•An, then biotin is a secondary binding partner for An. Similarly, biotin conjugated to a substance X (i.e., X-biotin) is a secondary binding partner for An if X-biotin•Av-$Ab_1$•An can form.

A hapten can function as a secondary binding partner. For example, a hybrid antibody can be prepared which binds the analyte An in one binding site and a hapten H to another. Thus, hapten H is then a secondary binding partner for An. If hapten H is first conjugated to some other substance X forming H-X, then H-X is a secondary binding partner for An if the complex An•Ab•H-X forms.

Similarly, if a nucleic acid analyte $NA_A$ is recognized by (hybridizes to) nucleic acid $NA_1$, forming the complex $NA_1$•$NA_A$, and nucleic acid $NA_2$ can further bind to this complex by binding to an unused part of $NA_1$, forming $NA_2$•$NA_1$•$NA_A$, then $NA_2$ is a secondary binding partner relative to $NA_A$.

Proteins such as antibodies, avidin, streptavidin, lectins, protein A, and protein G are commonly used as primary or secondary specific binding proteins. Related forms of these and other proteins are also used, e.g. the Fab, and $F(ab')_2$ parts of antibodies. Succinylavidin is another example.

Polymer-modified proteins may also be used as primary or secondary binding partners. Examples of the polymers employed in producing such polymer-modified proteins are other proteins, polypeptides, polysaccharides, polynucleotides, and synthetic polymers such as polyacrylic acid or polyacrcylylhydrazide. In use, the polymer on the polymer-modified protein carries many copies of a given release tag or of releasable SgCO groups, thus allowing the polymer-modified protein to be detected with high sensitivity. Similarly, polymer-modified polynucleotides can be prepared for detection with very high sensitivity.

Examples of primary and secondary binding partners which are conveniently labeled by the release tag compounds of the invention are a) proteins: for example, antibodies, avidin, streptavidin, lectins, protein A, and protein G;

b) polymer-modified proteins: for example, antibody-poly asp hydrazide, antibody-dextran, antibody-polyethyleneimine, antibody-dextran, avidin-dextran, and avidin-polyglu-hydrazide;

c) peptides: for example, angiotensin II;

d) polynucleotides: for example, complementary DNA and RNA;

e) polymer-modified polynucleotides: for example, 3'-tailed DNA and RNA, DNA-polyglu hydrazide, and DNA-dextran hydrazide;

f) carbohydrates: for example, glucose;

g) haptens: for example, digoxin, digoxigenin, and fluorescein; and h) biotin.

Many of the above-listed materials can function either as primary or secondary binding partners, depending on the assay being conducted.

Examples of enzyme substrates which may be labeled by the release tag compounds of the invention are: carbohydrates such as chitin and glycolchitin, dextran, glucose-6-phosphate, and galactose glycosides; lipids such as cholesterol esters; nucleotides such as ATP and AMP; polynucleotides such as DNA and RNA; peptides such as dipeptides and dipeptide esters; proteins such as albumin; and esters suck as p-nitrophenyl esters, phosphate esters, and carboxylic acid esters.

As explained above, the release tag compounds of the invention are capable of forming conjugates with a wide variety of other substances. Such conjugates are fully covalent materials in which at least one release tag compound is covalently linked to at least one other molecular moiety. Conjugates may thus be symbolized as (substance)$_u$(tag)$_t$ where the tag is a residue of a release tag which is covalently bound to the substance. The subscripts u and t indicate that depending on the particular release tags and substances chosen for the conjugate, conjugates may contain one release tag and one other substance to be labeled, one release tag and multiple other substances, one substance labeled by multiple release tags, and multiple substances labeled with multiple release tags. Where the release tag employed originally contained multiple reactive functional groups Rf, in the resulting conjugate not all of these are necessarily reacted with substance to be labeled. The substance being labeled may also possess multiple reactive functional groups initially, not all of which are necessarily reacted with release tag compounds in forming the conjugate.

The release tag compounds employed in forming conjugates of the invention must each have at least one signal group-containing unit SgCO-, and in release tag compounds of formula I will frequently have multiple such units. In release tag compounds bearing multiple signal groups and multiple reactive functional groups, the remaining portion of the molecule linking these together is generally relatively large, and may or may not be precisely definable.

In conjugates containing multiple release tag residues, these conjugates can be derived from the same or different release tag molecules. Similarly, where the conjugate contains multiple subunits, as in a protein possessing quaternary structure, these may also be the same or different.

The release tag compounds of the invention are synthesized using principles and reactions which are well known to those skilled in the art. They are prepared basically in three stages. In the first stage (stage one), molecular species containing the signal group Sg, the release group Re, and the reactivity group Rx in final or precursor form (i.e., carrying a protecting group) are obtained either commercially or via synthesis. The second stage (stage two) involves carrying out appropriate chemical reactions to join these materials into the release tag compound SgReRx which may, however, still contain certain functionalities in precursor or protected form. In the third stage (stage three), any such functionalities are converted to the desired final form.

Obtaining the signal groups Sg in stage one of the synthetic process generally involves preparation of electrophoric carboxylic acids such as trichloroacetic acid, which correspond to Sg—$CO_2H$. Many such carboxylic acids are known, and others may be prepared conveniently by reactions such as halogenation of precursor unsaturated carboxylic acids, and quenching with carbon dioxide of Grignard reagents prepared from halogenated hydrocarbons. When mixtures of halogenated carboxylic acids of varying halogen content or substitution pattern are generated in synthetic procedures, these can usually be fractionated chromatographically, to yield multiple signal group precursors from a given reaction.

For synthesis of the release tag compounds of formula I, many of the release groups are obtained in stage one in a precursor form. It is their coupling to the signal group-containing moiety Sg—$CO_2H$ which yields the final form of the release group. The release group precursors are typically such materials as simple amino acids, hydroxy acids, diamines, and similar difunctional molecules, many of which are commercially available. The second functional group in these molecules is required for the attachment of the reactivity group Rx.

The reactivity groups Rx or their precursors for stage three are generally commercially available because of the widespread usefulness of such reactivity groups in bio-organic chemistry.

For synthesis of the release tag compounds of formula II, where Re involves a diol, R-hydroxy ketone, or olefin, this functionality is established either before or after incorporation of the release group precursor into a release tag, by reactions such as oxidation, hydrolysis, elimination, the Wittig reaction, or combinations of these. More particularly, for the synthesis of the release tag compounds of formula II, one can make use of many of the reagents and reactions which allowed the first class to be prepared. For the formation of olefin and glycol release tags, the general strategy is to start with SgCOCl, and form the corresponding aldehyde by a reduction reaction, several of which have been described (March, J., *Advanced Organic Chemistry*, J. Wiley, New York, 3rd Edn., 1985, p. 396). The aldehyde can be converted into an olefin by a Wittig reaction ((a) House, H. O., Jones, V. K., Frank, G. A. *J. Org. Chem.* 1964 29, 3327; (b) House, H. O., Rasmusson, G. H. *Ibid*, 1961, 26, 4278; (c) Maercker, A., *Org. React.*, New York, 1965, 14, 270; (d) House, H. O., *Modern Synthetic Reactions*, 2nd Edn., W. A. Benjamin, Inc., Menlo Park, Calif., 1972, pp. 682–709.) or a Horner-Emmon's reaction (Reviews: (a) Boutagy, J. and Thomas, R., *Chem. Rev.* 1974, 74, 87; (b) Wadsworth, W. S., *Org. React.*, New York, 1977, 25, 73.) This establishes an olefin release group. In turn, a glycol release group can be formed by oxidizing the olefin with alkaline potassium permanganate, or osmium tetroxide in pyridine, or a peracid as described (House, H. O., *Ibid.*, pp. 275, 298). A reactivity group (Rx) is then incorporated as in the preparation of the first class of release tags, taking advantage of an appropriate functional group introduced in the Wittig reaction.

For hydroxyketo release tags, SgCOCl is reacted with an organocadmium compound, to form a corresponding ketone as has been reviewed (Cason, *Chem. Revs.*, 40, 1947, 15). The ketone in turn is brominated as described (House, *Ibid.*, 529) and hydrolyzed as described (Wagner, R. B. and Zook, H. D., *Synthetic Organic Chemistry*, John Wiley and Sons, New York, 1953, p. 170) to form the corresponding α-hydroxyketone. As desired, the α-hydroxy and keto groups can be reversed under acidic conditions (the α-ketol rearrangement) as has been described (March, *Ibid.*, p. 967). A reactivity group Rx is then incorporated as in the preparation of the first class of release tags.

Related procedures for synthesizing olefinic, glycol, and α-hydroxyketone release tags can be developed from standard reactions in organic chemistry by one skilled in the art.

The general literature on peptide synthesis is quite relevant to the preparation of release tag compounds. Release tags commonly utilize amide linkages, the formation of which is the heart of peptide synthesis. Protecting groups are also important in peptide synthesis and the same ones can be used as necessary for most if not all of the protections needed in release tag synthesis.

In Table XIII below are listed a number of representative electrophoric carboxylic acids Sg—$CO_2H$, as well as representative chemical reactions by which they may be formed from commercially available starting materials. Such materials serve as precursors of the Sg-containing portion of the release tags, the halogenated portions of the molecules being the ultimate signal groups Sg. Those skilled in the art will recognize that other starting materials can be subjected to the illustrated reaction conditions, and the illustrated starting materials can be subjected to reaction conditions other than those particularly shown, to yield yet additional electrophoric carboxylic acid products.

TABLE XIII

Preparation of Sg—$CO_2H$

| No. | Starting Material | Reactants | Product(SgCO$_2$H) |
|---|---|---|---|
| 1 | $CHCl_2$—COOH[1a] | Br$_2$/Red P | $CBrCl_2$—COOH |
| 2 | $CH_2I$—COOH[1a] | Cl$_2$/Red P | $CCl_2I$—COOH |
| 3 | $CH_2I$—COOH[1a] | Br$_2$/Red P | $CBr_2I$—COOH |
| 4 | $CFH_2$—COOH[1a] | Br$_2$/Red P | $CBr_2F$—COOH |
| 5 | $CFH_2$—COOH[1a] | Cl$_2$/Red P | $CCl_2F$—COOH |
| 6 | $CH_2Cl$—COOH[1a] | Br$_2$/Red P | $CBr_2Cl$—COOH |
| 7 | $CH_3COCO_2H$[1a] | PBr$_5$ | $CH_3CBr_2CO_2H$ |
| 8 | $CH_3COCO_2H$[1c] | PCl$_5$ | $CH_3CCl_2CO_2H$ |
| 9 | $CCl_2$=CCl—COOH[1d] | Cl$_2$/CCl$_4$ | $CCl_3$—$CCl_2$—COOH |
| 10 | $CCl_3$—CO—COOH[1g] | 1) NaBH$_4$<br>2) PCl$_5$<br>3) Br$_2$/Red P | $CCl_3$—CBrCl—COOH |
| 11 | $CCl_2$=CCl—COOH[1d] | Br—Cl | $CCl_3$—CClBr—COOH |
| 12 | $CCl_2$=CCl—COOH[1d] | Br$_2$/CCl$_4$ | $CBrCl_2$—CBrCl—COOH |
| 13 | $CCl_3$—CO—COOH[1d] | PBr$_5$ | $CCl_3$—CBr$_2$—COOH |
| 14 | $CH_2Cl$—CO—COOH[1c,h] | 1) Br$_2$Na$_2$CO$_3$<br>2) PCl$_5$ | $CClBr_2$—$CCl_2$—COOH |
| 15 | $CH_3$—CO—COOH[1a] | 1) Br$_2$/Na$_2$CO$_3$<br>2) PCl$_5$ | $CBr_3$—$CCl_2$—COOH |
| 16 | HC≡C—COOH[1f] | 1) Br$_2$/CCl$_4$<br>2) alc KOH<br>3) Cl$_2$/CCl$_4$ | $CClBr_2$—CClBr—COOH |
| 17 | $CH_2Br$—CO—COOH[1b,g] | 1) Cl$_2$/Na$_2$CO$_3$ | $CBrCl_2$—CBr$_2$—COOH |

TABLE XIII-continued

Preparation of Sg—CO$_2$H

| No. | Starting Material | Reactants | Product(SgCO$_2$H) |
|---|---|---|---|
| 18 | CH$_3$—CO—COOH$^{(1a)}$ | 1) Br$_2$/Na$_2$CO$_3$<br>2) NaBH$_4$<br>3) SOCl$_2$<br>4) Br$_2$/Red P | CBr$_3$—CBrCl—COOH |
| 19 | CCl$_2$=CCl—COOH$^{(1d)}$ | 1) Zn dust<br>2) Br$_2$ excess | CClBr$_2$—CBr$_2$—COOH |
| 20 | CH$_3$—CO—COOH$^{(1a)}$ | 1) Br$_2$/Na$_2$CO$_3$<br>2) PBr$_5$ | CBr$_3$—CBr$_2$—COOH |
| 21 | HC≡C—COOH$^{(1i)}$ | Cl$_2$/CCl$_4$ | HCl$_2$C—CCl$_2$—COOH |
| 22 | CCl$_3$—CO—COOH$^{(1g)}$ | 1) NaBH$_4$<br>2) PCl$_5$ | CCl$_3$—CHCl—COOH |
| 23 | CH$_2$Cl—CO—COOH$^{(1c,h)}$ | 1) Cl$_2$/Red P<br>2) NaBH$_4$<br>3) PCl$_5$<br>4) Br$_2$/Red P | CHCl$_2$—CClBr—COOH |
| 24 | CH$_2$Br—CO—CO$_2$H$^{(1b)}$ | 1) Cl$_2$/Red P<br>2) NaBH$_4$<br>3) PCl$_5$ | CCl$_2$Br—CHCl—COOH |
| 25 | CCl$_3$—CO—COOH$^{(1g)}$ | 1) NaBH$_4$<br>2) PBr$_5$ | CCl$_3$—CHBr—COOH |
| 26 | CH$_2$Cl—CO—COOH$^{(1c,h)}$ | 1) Br$_2$/Na$_2$CO$_3$<br>2) PCl$_5$ | CHBrCl—CCl$_2$—COOH |
| 27 | HC≡C—COOH$^{(1i)}$ | 1) 1 eq. Br$_2$/CCl$_4$<br>2) Cl$_2$ | CHBrCl—CBrCl—COOH |
| 28 | CH$_2$Br—CO—COOH$^{(1b)}$ | 1) 1 eq. Br$_2$/Na$_2$CO$_3$<br>2) PCl$_5$ | CHBr$_2$—CCl$_2$—COOH |
| 29 | CH$_2$Cl—CO—COOH$^{(1c,h)}$ | 1) 1 eq. Cl$_2$/Na$_2$CO$_3$<br>2) PBr$_5$ | CHCl$_2$—CBr$_2$—COOH |
| 30 | CH$_3$—CO—COOH$^{(1a)}$ | 1) Br$_2$/Na$_2$CO$_3$<br>2) NaBH$_4$<br>3) PCl$_5$ | CBr$_3$—CHCl—COOH |
| 31 | CH$_2$Cl—CO—COOH$^{(1a)}$ | 1) Br$_2$/Na$_2$CO$_3$<br>2) NaBH$_4$<br>3) PBr$_5$ | CBr$_2$Cl—CHBr—COOH |
| 32 | CH$_2$Br—CO—COOH$^{(1b,g)}$ | 1) 1 eq. Br$_2$/Na$_2$CO$_3$<br>2) NaBH$_4$<br>3) PCl$_5$<br>4) Br$_2$/Red P | CHBr$_2$—CBrCl—COOH |
| 33 | CH$_2$Cl—CO—COOH$^{(1b,g)}$ | 1) 1 eq. Br$_2$/Na$_2$CO$_3$<br>2) PBr$_5$ | CHBrCl—CBr$_2$—COOH |
| 34 | HC≡C—COOH$^{(1i)}$ | Br$_2$/CCl$_4$ | Br$_2$CH—CBr$_2$—COOH |
| 35 | CH$_3$—CO—COOH$^{(1a)}$ | 1) Br$_2$/Na$_2$CO$_3$<br>2) NaBH$_4$<br>3) PBr$_5$ | CBr$_3$—CHBr—COOH |
| 36 | CH$_2$Br—CO—COOH$^{(1b)}$ | 1) Cl$_2$/Na$_2$CO$_3$<br>2) PCl$_5$ | CCl$_2$Br—CCl$_2$—COOH |
| 37 | CH$_2$Br—CO—COOH$^{(1b)}$ | PCl$_5$ | CH$_2$Br—CCl$_2$—COOH |
| 38 | CH$_2$Br—CO—COOH$^{(1b)}$ | 1) Cl$_2$/Na$_2$CO$_3$<br>2) NaBH$_4$<br>3) PCl$_5$ | CHClBr—CHCl—COOH |
| 39 | CH$_2$Cl—CO—COOH$^{(1b)}$ | 1) NaBH$_4$<br>2) PBr$_5$<br>3) Cl$_2$/Red P | CH$_2$Cl—CClBr—COOH |
| 40 | CH$_2$Cl—CO—COOH$^{(1b)}$ | 1) 1 eq. Cl$_2$/Na$_2$CO$_3$<br>2) NaBH$_4$<br>3) PBr$_5$ | CHCl$_2$—CHBr—COOH |
| 41 | CH$_2$Br—CO—COOH$^{(1b)}$ | 1) Br$_2$/Red P<br>2) NaBH$_4$<br>3) PCl$_5$ | CHBr$_2$—CHCl—COOH |
| 42 | C$_6$H$_5$CH$_2$CO$_2$H$^{(1a)}$ | Br$_2$/Na$_2$CO$_3$ | C$_6$H$_5$CBr$_2$CO$_2$H |
| 43 | CH$_2$Cl—CO—COOH$^{(1b)}$ | 1) NaBH$_4$<br>2) H$^+$(—H$_2$O)<br>3) Br$_2$/CCl$_4$ | CHClBr—CHBr—COOH |
| 44 | CH$_2$Cl—CO—COOH$^{(1b)}$ | PBr$_5$ | CH$_2$Cl—CBr$_2$—COOH |
| 45 | C$_6$H$_5$CH$_2$CO$_2$H$^{(1a)}$ | Cl$_2$/Na$_2$CO$_3$ | C$_6$H$_5$CCl$_2$CO$_2$H |
| 46 | CH$_2$Br—CO—COOH$^{(1b)}$ | 1) NaBH$_4$<br>2) H$^+$(—H$_2$O)<br>3) Br$_2$/CCl$_4$ | CHBr$_2$—CHBr—COOH |
| 47 | CH$_2$Br—CO—COOH$^{(1b)}$ | PBr$_5$ | CH$_2$Br—CBr$_2$—COOH |
| 48 | CH$_2$Cl—CO—COOH$^{(1b)}$ | PCl$_5$ | CH$_2$Cl—CCl$_2$—COOH |
| 49 | CHCl$_2$—CHO$^{(1a)}$ | 1) HCN | CHCl$_2$—CHCl—COOH |

TABLE XIII-continued

Preparation of Sg—CO₂H

| No. | Starting Material | Reactants | Product(SgCO₂H) |
|---|---|---|---|
| | | 2) H₃O⁺Δ | |
| | | 3) PCl₅ | |
| 50 | C₁₀H₇CH₂CO₂H$^{(1a)}$ | Cl₂/Red P | C₁₀H₇CCl₂CO₂H |
| 51 | CCl₂=CCl—COOH$^{(1a)}$ | I—Cl | CCl₃—CICl—COOH + CCl₂I—CCl₂—COOH |
| 52 | CF₂=CF—COOCH₃$^{(1g)}$ | 1) Cl₂ 2) NaOH/H⁺ | CF₂Cl—CFCl—COOH |
| 53 | CF₂=CF—COOCH₃$^{(1g)}$ | 1) Br2 2) NaOH/H⁺ | CF₂Br—CFBr—COOH |
| 54 | CF₂=CF—COOCH₃$^{(1g)}$ | I—Cl | CF₂I—CFCl—COOH + CF₂Cl—CFI—COOH |
| 55 | C₁₀H₇CH₂CO₂H$^{(1a)}$ | Br₂/Red P | C₁₀H₇CBr₂CO₂H |
| 56 | CH₂F—CO—COOH$^{(1k)}$ | 1) Cl₂/Red P 2) PCl₅ | CCl₂F—CCl₂—COOH |
| 57 | CH₂F—CO—COOH$^{(1k)}$ | 1) Cl₂/Red P 2) NaBH₄ 3) PCl₅ | CCl₂F—CHCl—COOH |
| 58 | CH₂F—CO—COOH$^{(1k)}$ | 1) Cl₂/Red P 2) NaBH₄ 3) SF₄ | CCl₂F—CHF—COOH |
| 59 | CF₃—CH₂—CH₂OH$^{(1f)}$ | 1) K₂Cr₂O₇/H⁺ 2) Cl₂/Red P | CF₃—CCl₂—COOH |
| 60 | CF₃—CH₂—CH₂OH$^{(1f)}$ | 1) K₂Cr₂O₇/H⁺ 2) Cl₂ leq./Red P | CF₃—CHCl—COOH |
| 61 | CF₃—CH₂—CH₂OH$^{(1f)}$ | 1) K₂Cr₂O₇/H⁺ 2) Br₂/Red P | CF₃—CBr₂—COOH |
| 62 | CH₂F—CO—COOH$^{(1f)}$ | 1) Cl₂/Red P 2) PBr₅ | CCl₂F—CBr₂—COOH |
| 63 | CH₂F—CO—COOH$^{(1f)}$ | 1) Br₂/Red P 2) PBr₅ | CBr₂F—CBr₂—COOH |
| 64 | CH₂F—CO—COOH$^{(1f)}$ | 1) Br₂/Red P 2) NaBH₄ 3) SF₄ | CBr₂F—CHF—COOH |
| 65 | CH₂F—CO—COOH$^{(1f)}$ | 1) Br₂/Red P 2) HCN 3) PCl₅ | CBr₂F—CCl(CN)—COOH |
| 66 | NC—CH₂—COOH$^{(1b,a)}$ | Cl₂/Red P | NC—CCl₂—COOH |
| 67 | NC—CH₂—COOH$^{(1b,a)}$ | Br₂/Red P | NC—CBr₂—COOH |
| 68 | NC—CH₂—CH₂—COOCH₃$^{(1e)}$ | 1) Cl₂/Red P 2) NaOH/H⁺ | NC—CH₂—CCl₂—COOH |
| 69 | NC—CH₂—CH₂—COOCH₃$^{(1e)}$ | 1) Br₂/Red P 2) NaOH/H⁺ | NC—CH₂—CBr₂—COOH |
| 70 | CCl₃—CO—COOH$^{(1e)}$ | 1) KCN/H⁺ 2) PCl₅ | CCl₃—CCl(CN)—COOH |
| 71 | CCl₃—CO—COOH$^{(1e)}$ | 1) KCN/H⁺ 2) PBr₅ | CCl₃—CBr(CN)—COOH |
| 72 | CCl₃—CO—COOH$^{(1e)}$ | 1) KCN/H⁺ 2) SF₄ | CCl₃—CF(CN)—COOH |
| 73 | CH₃—CO—COOH$^{(1e)}$ | 1) Br₂/Na₂CO₃ 2) KCN/H⁺ 3) PCl₅ | CBr₃—CCl(CN)—COOH |
| 74 | HC≡C—COOH$^{(1l)}$ | 1 mole Br₂ | Br—CH=CBr—COOH |
| 75 | HC≡C—COOH$^{(1l)}$ | 1 mole Cl₂ | CHCl=CCl—COOH |
| 76 | HC≡C—COOH$^{(1l)}$ | 1) Br₂/CCl₄ (excess) 2) NaNH₂ | Br₂C=CBr—COOH |
| 77 | HC≡C—COOH$^{(1l)}$ | 1) 1 mole Cl₂ 2) Br₂ 3) alc KOH | ClBrC=CCl—COOH + ClBrC=CBr—COOH |
| 78 | 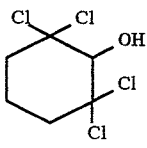 (1a) | 1) K₂Cr₂O₇/H⁺ 2) KCN/H⁺ 3) H₃O⁺ 4) PCl₅ | 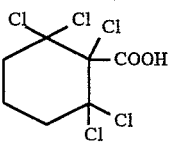 |
| 79 | CCl₂=CCl—COOH$^{(1a)}$ | CHCl₃/KtOBu | 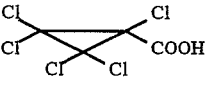 |

TABLE XIII-continued

Preparation of Sg—CO₂H

| No. | Starting Material | Reactants | Product(SgCO₂H) |
|---|---|---|---|
| 80 | [cyclobutane structure with F substituents and CH₂OH] (1g) | 1) K₂Cr₂O₇/H⁺<br>2) MeOH/H⁺<br>3) NaOEt/Cl₂<br>4) NaOH/H⁺ | [cyclobutane structure with F substituents, Cl, and COOH] |
| 81 | [cyclohexane structure with F substituents and OH] (1g) | 1) K₂Cr₂O₇/H⁺<br>2) HCN<br>3) H₃O⁺<br>4) PCl₅ | [cyclohexane structure with F substituents, Cl, and COOH] |
| 82 | $Cl_2C=CClCO_2H^{(1d)}$ | Zn dust/heat | $ClC\equiv CCO_2H$ |
| 83 | $HC\equiv CH$, $HCOCO_2CH_2CH_3^{(1a)}$ | 1. NaNH₂<br>2. H₃O⁺<br>3. PCl₅<br>4. NaOH<br>5. H₃O⁺ | $HC\equiv C-CHCl-CO_2H$ |
| 84. | $CF_3CH_2Br^{(1i)}$ | 1. CdCl₂<br>2. ClCOCO₂Et<br>3. NaOH<br>4. Cl₂/Red P | $CF_3CCl_2COCO_2H$ |
| 85. | $N\equiv CCH_2OH^{(1m)}$ | 1. PI₂<br>2. CdCl₂<br>3. ClCOCO₂Et<br>4. NaOH<br>5. Cl₂/Red P | $N\equiv C-CCl_2COCO_2H$ |
| 86. | $HC\equiv CCHClCO_2Et^{(1m)}$ | 1. Br₂<br>2. NaOH | $BrHC=CBrCHClCO_2H$ |

Footnotes to TABLE XIII:
Starting material sources:
[1a]Aldrich Chemical Company
[1b]Morton Thiokol, Alfa Products
[1c]Biochemical Laboratories, Inc.
[1d]Columbia Organic Chemicals
[1e]CTC Organics
[1f]Interchemical Corporation
[1g]K&K Laboratories
[1h]Mide Chemical Corporation
[1i]Pfaltz and Bauer, Inc.
[1j]Reliable Chemical Company
[1k]United State Biochemical Corporation
[1l]Wiley Organic
[1m]Alfa
2) Many other electrophoric carboxylic acids are listed in Beilstein.

the initially prepared electrophoric carboxylic acid Sg—CO₂H is frequently further converted into another generally more reactive derivative for reaction with the precursor of the release group. Thus, for example, the carboxylic acid can be reacted with thionyl chloride, phosphorus pentachloride, or oxalyl chloride to yield the corresponding acid chloride. The anhydride of the carboxylic acid may be obtained by reacting the acid chloride with trichlorotrifluoro acetone hydrate in dry benzene in the presence of pyridine. Alternatively, the anhydride may be prepared by treating the carboxylic acid directly with $P_2O_5$ or acetic anhydride in refluxing benzene. The carboxylic acid may be converted to the corresponding aldehyde as described by Harrison, I. T., and Harrison, S., Compendium of Organic Synthetic Methods, Wiley-Interscience, New York, 1971, pp. 132–137. Additional methods are provided in Volumes 1 through 5 of this series. See for example Wade, L. G., Volume 5, pp. 93–96, 1984. The aldehyde Sg—CHO may be converted to the corresponding acetal Sg—CH(OR)₂ by an acid catalyzed reaction with an alcohol ROH. The α-keto acid Sg—CO—CO₂H may be prepared by reacting the acetal Sg—CH(OR)₂ with HCN, followed by reaction with sulfuric acid in water, and finally with chromium oxide. This α-keto acid may in turn be converted to the corresponding acid chloride by reaction with thionyl chloride or other reagents as discussed above. The above-described carboxylic acid Sg—CO₂H or one of its reactive derivatives as discussed above is employed in a subsequent reaction with the precursor of the release group Re in the synthesis of the desired release tag compounds.

The volatile compound derived from the $S_g$ moiety in a release tag is detected preferably by an electron capture detector (ECD) or by electron capture negative ion mass spectrometry (ECNI-MS). Examples of other gas phase detectors that may be used are as follows: flame ionization detector, electron impact MS, positive ion chemical ionization MS, thermospray MS, fast atom bombardment MS, fast ion bombardment MS, atmospheric pressure ionization MS, particle beam MS, electrospray MS, plasma desorption MS, laser ionization MS, laser desorption MS, thermal conductivity detector, nitrogen-phosphorous detector, photoionization detector, flame photometric detector, and ion mobility detector.

EXPERIMENTAL

Rotary—flash injector

An injector assembly was prepared by connecting a Varian rotary valve assembly (part No. 03-908719-00) to the front end of a Varian flash injector body (part No. 01-001014-00) by means of a nut bored with opposite threads at each end to accept and connect the valve assembly and the injector body, respectively. This nut was provided with a gas inlet line for introduction of carrier gas.

Within the flash injector body was placed a glass insert tube which extended from the top end of the injector body and out the bottom end. This glass insert was 130 mm in length and 6 mm OD, and fit closely in the bore of the injector body. The first 2.6 cm of the glass insert had an inside diameter of 4 mm, and the remainder of the insert possessed a 2 mm bore. At the juncture of the 4 mm and 2 mm ID portions of the glass insert was placed a plug of clean glass wool.

The injector assembly was mounted on a Varian Model 6000 GC equipped with an electron capture detector, the injector body being housed in a heated injector block (Varian part No. 62-000203-00). The lower end of the glass insert was connected to a capillary GC column, the front end of which was placed within the glass liner approximately 80 mm -from its outlet end. The outlet end of the flash injector body was located at the top of the column oven of the gas chromatograph.

Chromatography

The chromatographic column was a 0.32 mm ID×7 m Quadrex 007 column (5% phenyl methyl silicone; Quadrex, Inc.), 5 μm film thickness. 1 μl injections of sample solutions were made onto the glass wool in the glass insert, with a 5 μl syringe fitted with an 11.5 cm stainless steel needle, the injector body being maintained at 300° C. and the column being at a low temperature such as 50° C. After sample injection, the column was held at its initial temperature for about three minutes, then programmed quickly at 50° C./min to 150° C., and held at this temperature for five minutes. Nitrogen flow through the column was 3 ml/min, measured at RT, with the column at 50° C. The detector was maintained at 310° C.

WORKING EXAMPLES

N-Trichloroacetyl-p-aminobenzoic acid (CCl$_3$CO-ABA) (W1).

p-Aminobenzoic acid (1 g, 7.3 mmol) and 7 mL (32.8 mmol) of trichloroacetic anhydride were refluxed for 0.5 hr. More anhydride (3 mL) was added and heating was continued for 16 hr. Water (15 mL) and ethyl acetate (30 mL) were added, and, after shaking, the separated organic layer was dried (anhyd. Na$_2$SO$_4$) and evaporated (rotary evaporator) to give the product as yellowish white crystals. The product was a single spot by TLC (silica; ethyl acetate/hexane, ⅔), and its structure was confirmed by its spectral characteristics.

N-Trichloroacetyl-p-aminobenzoic acid N-hydroxysuccinimide ester (CCl$_3$CO-AB-NHS) (W2).

Compound W1 (290 mg, 1.03 mmol) was dissolved in 5 mL of dimethylformamide (DMF) and the temperature was raised to 70° C. N,N-(carbonyldiimidazole (144 mg,, 0.90 mmol) was added, and 70° C. was continued until CO$_2$ evolution ceased (30 min). N-Hydroxysuccinimide (102 mg, 0.09 mmol) was added, heating was discontinued, and the reaction mixture was stirred for 17.5 hr. The solvent was removed under high vacuum, and the addition of 15 mL of isopropanol gave a white precipitate (304 mg, 81%) which was a single spot by silica TLC (2:3 ethyl acetate:hexane, v/v), and which melted at 258° C. After recrystallization from isopropanol, the structure of the product was confirmed by MS, IR, and $^1$H NMR.

N-Trichloroacetyl-N-methyl-p-aminobenzoic acid (CCl$_3$CO-MABA)(W3).

4-(Methylamino)benzoic acid (1.00 g, 6.62 mmoL) and trichloroacetic anhydride (3.07 g, 9.94 mmoL) were refluxed in 20 mL of dry benzene for 30 min. After evaporation and flash column chromatography (ethyl acetate/hexane 3/7 v/v), the product was obtained as a white solid (1.1 g, 56%), the structure of which was confirmed by its spectral characteristics.

N-Trichloroacetyl-N-methyl-p-aminobenzoic acid N-hydroxysuccinimide ester (CCl$_3$CO-MAB-NHS)

Compound W3 (285.5 mg, 0.96 mmol) and N,N-carbonyldiimidazole (156 mg, 0.96 mmol) were heated with stirring at 70° C. in 5 mL of dimethylformamide until no more CO$_2$ evolved (10 min). After the heat was removed, stirring was continued for 30 min, N-hydroxysuccinimide (111 mg, 0.96 mmol) was added and the reaction mixture was stirred at RT for 17 hr. The solid residue was purified by recrystallization from isopropanol, yielding a white solid (250 mg, 66%), m.p. 183° C., the structure of which was confirmed by its spectral characteristics.

Trichloroacetylmethylaminobenzoyl-Albumin (CCl$_3$CO-MAB-Albumin) (W5).

Bovine Serum Albumin (BSA, 1 mg; Sigma Chemical Co.) was dissolved in 1 mL of potassium phosphate buffer, pH 8 and 1.74 mg of compound W4 dissolved in 100 μL of dimethylsulfoxide was added, followed by stirring at RT for 17 hr. The resulting solution was dialyzed against 4×1 L of 0.01 M ammonium bicarbonate at 4° C. over a period of 3 d. Based on the TNBS test, 74% of the amino groups in BSA had been modified with 4.

Diaminooctyl-DNA(DAO-DNA) (W6).

Sodium bisulfite was prepared by adding 3.15 g of sodium sulfite and 7.15 g of sodium metabisulfite to 25 ml of water. 1,8-Diaminooctane (7.2 g) was added and the pH was adjusted to 7 with concentrated hydrochloric acid. Calf thymus DNA (Sigma, 139 mg) was dissolved in 20 mL of water and denatured by heating to 100° C. for 30 min followed by rapid cooling in an ice bath. The single stranded DNA was then sonicated for 40 min at 0° C. and added to the sodium bisulfite-diaminooctene solution. This gave a final concentration of 2 M bisulfite and 1 M diaminooctane. The mixture was clarified by centrifugation (4000×g) and then stirred at 60° C. (oil bath) for 42 hrs. The reaction mixture was cooled and filtered (0.2 μm filter) to remove a small amount of particulate material. The product was desalted in two 25 mL portions over a BioRad P-4 column (340×2.6 cm) equilibrated in 0.02 M sodium chloride, 1 mM EDTA, pH 8. After the void volume (60 mL), the product was collected in the next 50 mL fraction and each of these two fractions was separately dialyzed overnight against 4 L of water and lyphilized, yielding together 99.5 mg (72%). Seventy-five percent of the cytosine residues were substituted with DAO, based on alkaline hydrolysis-HPLC.

N-Trichloroacetyl-p-aminobenzoyl-BSA(CCl₃CO-AB-BSA) (W7)

N-Trichloroacetyl-p-aminobenzoic acid NSH ester (16.6 mg, 0.04 mmol, Compound W2) was added in small portions over 15 min to a solution of 2 mg (0.02 µmol) of bovine serum albumin (BSA) in a 1.8 mL of a 0.1 M potassium phosphate buffer, pH 8/DMSO, 1:1, followed by stirring for 18 h at room temperature. This solution was centrifuged and the clear supernatant was passed through a PD10 column (Pharmacia) 2 times using 0.01 M KPB, pH 8.0, followed by lyophilization. Protein analysis (BCA test; Pierce Chemical Co.) and amino group analysis by a trinitrobenzene sulfonic acid (TNBS) test indicated that 82% of the primary amino groups on BSA were modified.

N-Trichloroacetyl-p-aminobenzoyl-DAO-/DNA (CCl₃CO-AB-DAO-DNA) (W8)

Formamide/DMSO (700 µL, 4:3) containing 15 mg (0.038 mmol) of N-trichloroacetyl-p-aminobenzoic acid NSH ester (W2) was added dropwise to a solution of DAO-DNA in 800 µL of 0.1 M KPB pH 8. The resultant cloudy solution (precipitation of the DAO-DNA by the organic solvent) was stirred at room temperature for 18 h. The reaction mixture was centrifuged and the clear supernatant was passed through a PD10 column twice using 0.01 M KPB pH 8 followed by lyophilization.

Enzymatic digestion and HPLC analysis of modified DAO-DNA,

A sample of lyophilized CCl₃CO-AB-DAO-DNA (W8) was dissolved in 2.5 mL of Tris buffer pH 8.8 (0.025 M, 1 mM EDTA) and passed through PD10 column using the same buffer. To 1.5 mL of this solution, containing approximately 37 µg of CCl₃CO-AB-DAO-DNA based on $A_{260}$ was added 30 µL of 1 M CaCl₂ solution and 50 µg of staphylococcal nuclease (Sigma), followed by incubation at 37° C. for 3 h. HPLC analysis (C18-silica) showed a 66% disappearance of DAO-cytidylic acid and related peaks when compared against standard DAO-DNA treated similarly.

N-Trichloroacryloyl-p-aminobenzoic acid (CCl₂CClCO-ABA) (W9)

Trichloroacrylic acid (500 mg, 2.85 mmol; Alpha Chem. Co.) was added to 7 mL of SOCl₂ and the mixture was refluxed for 6 h. After cooling, 5 mL of benzene was added and the solvent was concentrated on the rotary evaporator to ⅓ of its original volume. This step was repeated 4 times, until most of SOCl₂ was evaporated. Three mL of acetonitrile were added followed by a suspension of 383 mg (2.80 mmol) of p-amino-benzoic acid in 3 mL of acetonitrile. After 30 min of stirring, TLC showed the disappearance of most starting material and the presence of a product with higher $R_f$ value. The product was purified by preparative silica TLC (EtOAC/Hexane/acetic acid, 2:3:0.05) which gave a pure white powder (89% yield); MS (EI) m/z 293 (M⁺).

Aqueous stability test of N-Trichloroacryloyl-p-aminobenzoic acid (W9)

N-Trichloroacryloyl-p-aminobenzoic acid (440 µg) was dissolved in 1 mL of methanol, and 100 µL of this solution was added to 300 µL of potassium phosphate buffer (0.1 M, pH 8). In the same way a solution of p-aminobenzoic acid was prepared. Both solutions were analyzed by HPLC (C18-silica column, 0.01 M potassium phosphate buffer pH 4.5 initially, then 0 to 38% acetonitrile over 29 minutes. This gave a retention time of 6.8 min for p-aminobenzoic acid and 26 min for the product. The solutions were kept at room temperature. Analysis by HPLC demonstrated that the N-trichloroacryloyl-p-aminobenzoic acid was stable at least for four days. By this last day the solution of the p-aminobenzoic acid had discolored and additional peaks were seen.

N-Trichloroacryloyl-p-aminobenzoic acid N-hydroxysuccinimide ester (CCl₂CClCO-AB-NHS) (W10)

Dicyclohexylcarbodiimide (10 mg, 0.05 mmol) was added as a solid to a stirred suspension of N-trichloroacryloyl-p-aminobenzoic acid (14 mg, 0.047 mmol) and N-hydroxysuccinimide (5.98 mg, 0.05 mmol) in 3 mL of dry CH₂Cl₂ at 0° C. The reaction mixture was stirred under N₂ for 3 h and allowed to come to room temperature. The insoluble dicyclohexylurea was filtered, and rotary evaporation of the filtrate yielded a white solid. The product was purified by TLC using ETOAc:hexane:acetic acid (2:3:0.05). NMR indicated the presence of 4 methylene hydrogens at δ 3.0. MS (EI) 390 (M⁺) and 276 (base peak).

N-Trichloroacryloyl-p-aminobenzoyl-BSA (CCl₂CClCO-AB-BSA)

NSH ester W10 (22 mg) was added as a solid to 5 mg of bovine serum albumin (BSA) dissolved in 2.5 mL of 0.1 M potassium phosphate buffer, pH 8/dimethylsulfoxide, 60:40. The immediate white suspension was stirred overnight at room temperature. After centrifugation the clear supernatant was passed through a PD10 column twice, then lyophilized. A protein assay (Pierce BCA) and TNBS test indicated that 52% of the BSA amino groups had been modified.

N-Trichloroacryloyl-p-aminobenzoyl-DAO-DNA (CCl₂CClCO-AB-DAO-DNA)

NSH ester W10 (19 mg, 48 µmol) in 300 µL of DMF was added dropwise to 1 mL of a cold, stirring solution of DAO-DNA (2.7 mg) in 0.1 M KPB, pH 8. The reaction mixture was allowed to come to room temperature, 1.6 mL of DMF was added to give a clear solution, and stirring was continued for 18 h. After centrifugation, the clear supernatant was passed through a PD10 column and lyophilized. Digestion and HPLC analysis showed the disappearance of the DAO-cytidylic acid peaks and the presence of new peaks derived from the modification.

Detection of CCl₃CO-AB-BSA by GC-ECD

Figure 1B:
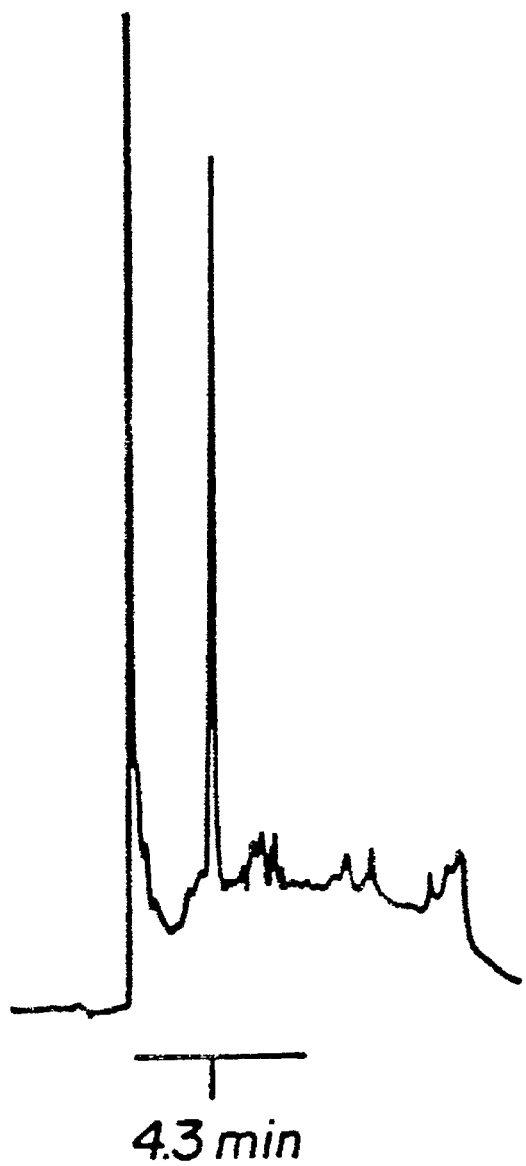
FIG. 1B shows a chromatogram from the injection of $2.7 \times 10^{-13}$ moles of $CCl_3CO$-AB-BSA.

The conjugate CCl₃CO-AB-BSA (W6) was dissolved in water and dilutions were made giving concentrations of this conjugate ranging from $2.4 \times 10^{-16}$ to $6 \times 10^{-13}$ mole/µL. Injection of 1 µL volumes of these solutions into the GC-ECD each gave a peak for chloroform, the released electrophore. Injection of water or a solution of albumin in water gave no peak for chloroform. The resulting standard curve is shown in FIG. 1A, including an inset presenting a chromatogram for the smallest amount of CCl₃CO-AB-BSA injected. In FIG. 1B is shown a chromatogram from the injection of $2.7 \times 10^{-13}$ mole of CCl₃CO-AB-BSA. Each injection was made over a 10 sec interval into the rotary-flash injector described above.

CCl₃CO-AB-BSA may also be detected by headspace injection GC-ECD in which an aqueous sample of CCl₃CO-AB-BSA is heated and the vapor, containing chloroform, is injected into a GC-ECD. The released chloroform may also be determined by electron capture negative ion mass spectrometry or by ion mobility spectrometer detector. $CCl_3CO$-AB-BSA may also be detected by heating an aqueous sample of $CCl_3CO$-AB-BSA and extracting the released chloroform in isooctane, toluene or a related organic solvent for injection into a GC-ECD.

Detection of $CCl_2ClCO$-AB-BSA by GC-ECD

An aqueous solution of $CCl_2ClCO$-AB-BSA was heated at 60° C. for 1 hr to enhance the aggregation of the $CCl_2ClCO$-AB-BSA. Injection as above of 1 μL of this solution into a GC-ECD gave a peak for $CCl_2ClH$.

Detection of $CCl_3CO$-AB-DAO-DNA by GC-ECD

To an aqueous solution of $CCl_3CO$-AB-DAO-DNA was added polylysine (Sigma) for the purpose of developing aggregates of these two substances. Injection as above of 1 μL of this solution into a GC-ECD gave a peak for $CHCl_3$.

Figure 2:
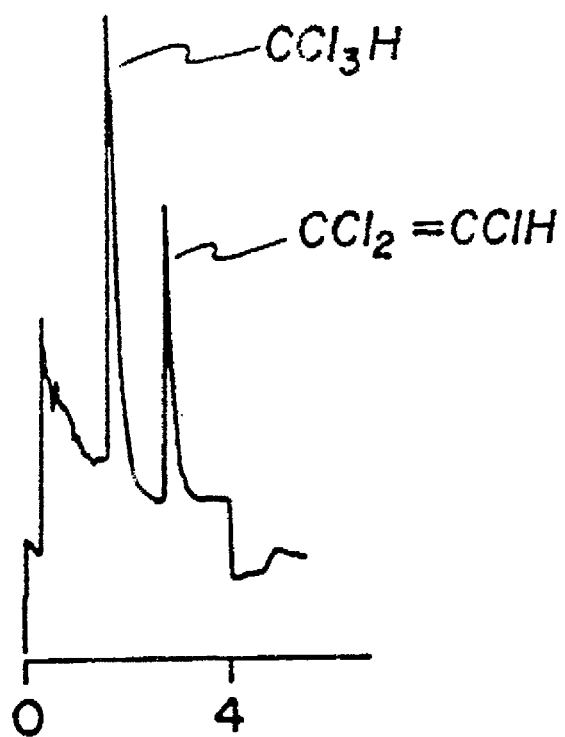
FIG. 2 shows a chromatogram with peaks for $CCl_3H$ and $CCl_2lCClH$ resulting from injection of a mixture of 331 ng of the release tag conjugate $CCl_2CClCO$-AB-BSA and 147 ng of the conjugate $CCl_3CO$-AB-DAO-DNA.

Detection of a mixture Of $CCl_2ClCO$-AB-BSA and $CCl_3CO$-AB-DAO-DNA by GC-ECD One μL of an aqueous solution containing 331 ng of $CCl_3CO$-AB-DAO-DNA, 334 ng of polylysine, 147 ng of $CCl_2ClCO$-AB-BSA, and 19.3 ng of albumin was injected as above into a GC-ECD. This gave the chromatogram shown in FIG. 2, displaying peaks for $CCl_3H$ and $CCl_2ClH$.

GC-ECD Of 2,2-Dichloropropionic Acid

Injection as above of one μL of water containing 2.78 ng of 2,2-dichloropropionic acid (Aldrich Chem. Co.) into a GC-ECD gave a peak for 1,1-dichloroethane.

Determination Of Ethanol by Thermal Release of an Electrophore

Ethanol is reacted with trichloroacetic anhydride to yield ethyltrichloroacetate.

The ethyltrichloroacetate was dissolved in water (2.76 ng/μl) and 1 μL was injected into a GC-ECD as above. A peak for chloroform was obtained.

PREDICTIVE EXAMPLES

The following examples illustrate signal groups Sg such as those shown in Table XIII, release groups, reactivity groups, and connecting moieties in a variety of release tag compounds, and provide suggested synthetic procedures for preparation of these compounds. Release tags which are illustrated in the form of carboxylic acids would generally be employed in practice as more reactive carboxylic acid derivatives such as N-hydroxy succinimide or benzotriazole esters, anhydrides, or acid chlorides, etc.

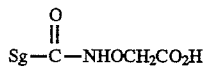  (1)

Carboxymethoxylamine-hydrochloride (Aldrich) is reacted with an anhydride of an electrophoric carboxylic acid $SgCO_2H$ such as those shown in Table XIII to afford the product.

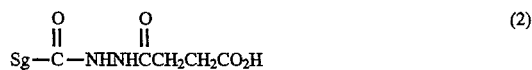  (2)

An anhydride of an electrophoric carboxylic acid $SgCO_2H$ such as those shown in Table XIII is reacted with hydrazine to form an SgCO-substituted hydrazine, which in turn is reacted with succinic anhydride to afford the product.

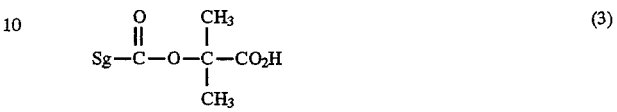  (3)

2-Hydroxyisobutyric acid (Aldrich) is combined with an acid chloride of an electrophoric carboxylic acid $SgCO_2H$ such as those shown in Table XIII in the presence of pyridine to afford the product.

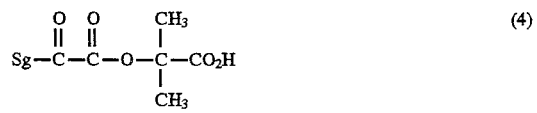  (4)

The diethyl acetal of an aldehyde corresponding to an electrophoric carboxylic acid $SgCO_2H$ such as those shown in Table XIII is reacted with hydrogen cyanide (generated from sodium cyanide plus sulfuric acid), followed by heating in aqueous sulfuric acid to afford the carboxylic acid corresponding to the intermediate α-hydroxy nitrile. This product is oxidized with chromic oxide in pyridine or acetic acid to give the 2-oxo-carboxylic acid, which is in turn reacted with thionyl chloride to afford the 2-oxo-carboxylic acid chloride. This is finally reacted with 2-hydroxyisobutyric acid in pyridine to afford the desired product.

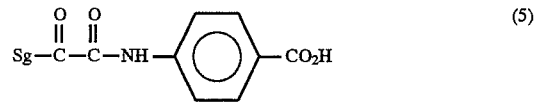  (5)

An acid chloride of an electrophoric 2-oxo-carboxylic acid $SgCOCO_2H$ (prepared as above in connection with (4)) is reacted with p-aminobenzoic acid to give the product.

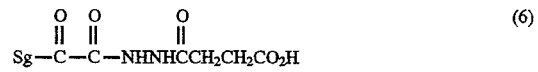  (6)

An acid chloride of an electrophoric 2-oxo-carboxylic acid $SgCOCO_2H$ (prepared as above in connection with (4)) is reacted with hydrazine to give the corresponding substituted hydrazine, which is reacted in turn with succinic anhydride to give the product.

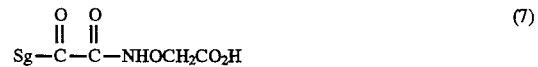  (7)

Carboxymethoxylamine hydrochloride is reacted with an acid chloride of an electrophoric 2-oxo-carboxylic acid $SgCOCO_2H$ (prepared as above in connection with (4)) to give the product.

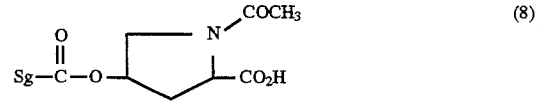  (8)

N-Acetylhydroxyproline (Sigma) is reacted with an acid chloride of an electrophoric carboxylic acid $SgCO_2H$ such as those shown in Table XIII in the presence of pyridine to give the product.

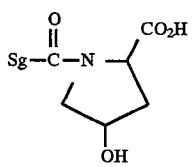 (9)

Hydroxyproline (Sigma) is reacted with an anhydride of an electrophoric carboxylic acid $SgCO_2H$ such as those shown in Table XIII to give the product.

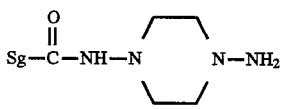 (10)

1,4-Diaminopiperazine is reacted with one equivalent of an anhydride of an electrophoric carboxylic acid $SgCO_2H$ such as those shown in Table XIII to yield the monosubstituted SgCO-1,4-diaminopiperazine.

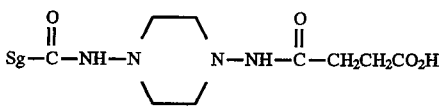 (11)

1,4-Diaminopiperazine is reacted with one equivalent of an anhydride of an electrophoric carboxylic acid $SgCO_2H$ such as those shown in Table XIII to yield the monosubstituted SgCO-1,4-diaminopiperazine. This compound is reacted in turn with succinic anhydride to give the product.

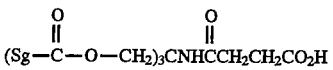 (12)

Tris-(Hydroxymethyl)aminomethane (Aldrich) is reacted with succinic anhydride to give N-succinyl-tris-(hydroxymethyl)-aminomethane, which in turn is reacted with an acid chloride of an electrophoric carboxylic acid $SgCO_2H$ such as those shown in Table XIII in pyridine to give the product.

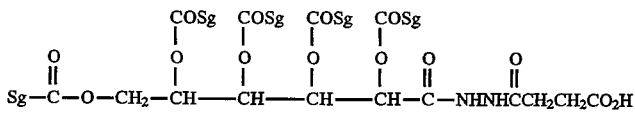 (13)

Gluconic acid lactone (Sigma) is reacted with hydrazine to yield gluconylhydrazide, which is reacted in turn with succinic anhydride to yield N-gluconyl-N'-succinylhydrazine. This latter compound is reacted with an acid chloride of an electrophoric carboxylic acid $SgCO_2H$ such as those shown in Table XIII in pyridine to yield the product.

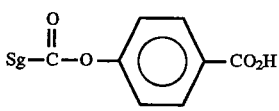 (14)

p-Hydroxybenzoic acid is reacted with an acid chloride of an electrophoric carboxylic acid $SgCO_2H$ such as those shown in Table XIII in pyridine to give the product.

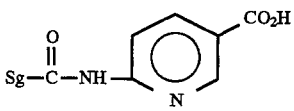 (15)

6-Aminonicotinic acid (Aldrich) is reacted with an anhydride of an electrophoric carboxylic acid $SgCO_2H$ such as those shown in Table XIII to give the product.

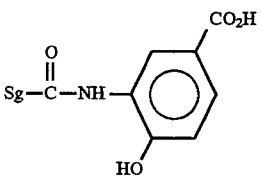 (16)

3-Amino-4-hydroxybenzoic acid (Aldrich) is reacted with an anhydride of an electrophoric carboxylic acid $SgCO_2H$ such as those shown in Table XIII to give the product.

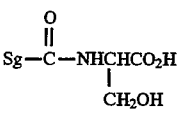 (17)

Serine (Sigma) is reacted with an anhydride of an electrophoric carboxylic acid $SgCO_2H$ such as those shown in Table XIII to give the product.

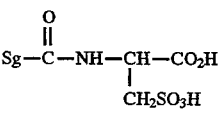 (18)

Cysteic acid (Sigma) is reacted with an anhydride of an electrophoric carboxylic acid $SgCO_2H$ such as those shown in Table XIII to give the product.

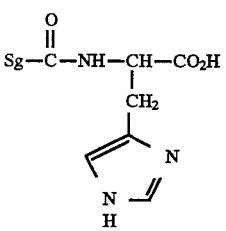 (19)

Histidine (Sigma) is reacted with an anhydride of an electrophoric carboxylic acid $SgCO_2H$ such as those shown in Table XIII to give the product.

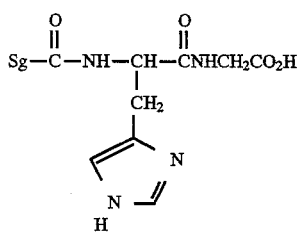 (20)

Histidylglycine (Sigma) is reacted with an anhydride of an electrophoric carboxylic acid SgCO₂H such as those shown in Table XIII to give the product.

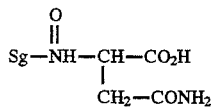 (21)

Asparagine (Sigma) is reacted with an anhydride of an electrophoric carboxylic acid SgCO₂H such as those shown in Table XIII to give the product.

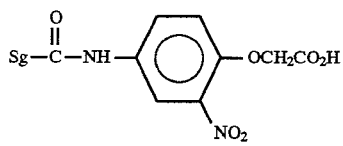 (22)

4-Amino-2-nitrophenol (Aldrich) is reacted with an anhydride of an electrophoric carboxylic acid SgCO₂H such as those shown in Table XIII to form the corresponding N-SgCO-substituted-4-amino-2-nitrophenol, which is reacted in turn with iodoacetate to give the product.

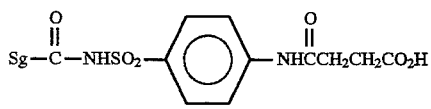 (23)

Sulfanilamide (Aldrich) is reacted with succinic anhydride to form 4-(succinamido)-sulfanilamide, which in turn is reacted with an acid chloride of an electrophoric carboxylic acid SgCO₂H such as those shown in Table XIII to give the product.

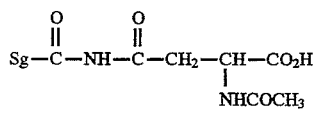 (24)

N^α-Acetylasparagine (Sigma) is reacted with an acid chloride of an electrophoric carboxylic acid SgCO₂H such as those shown in Table XIII to give the product.

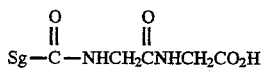 (25)

Glycylglycine is reacted with an anhydride of an electrophoric carboxylic acid SgCO₂H such as those shown in Table XIII to give the product.

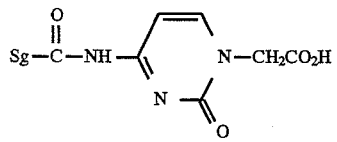 (26)

Cytosine (Sigma) is reacted with an anhydride of an electrophoric carboxylic acid SgCO₂H such as those shown in Table XIII to give the corresponding N-SgCO-substituted cytosine, which is reacted in turn with iodoacetate to give the product.

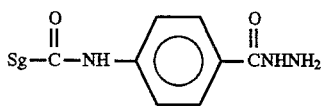 (27)

p-Aminobenzoic acid is reacted with an acid chloride or anhydride of an electrophoric carboxylic acid SgCO₂H such as those shown in Table XIII to yield the N-SgCO-substituted carboxylic acid, which is in turn activated with N,N-carbonyldiimidazole then reacted with N-hydroxysuccinimide to produce the N-hydroxysuccinimide ester of the carboxylic acid. This is finally reacted with hydrazine to give the product.

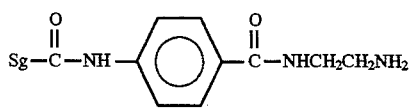 (28)

The N-SgCO-substituted-p-aminobenzoic acid prepared as an intermediate in the synthesis of 27 above is reacted with ethylene diamine to give the product.

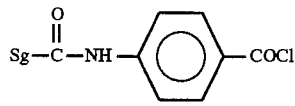 (29)

The N-SgCO-substituted-p-aminobenzoic acid prepared as an intermediate in the synthesis of 27 above is reacted with thionyl chloride to give the product.

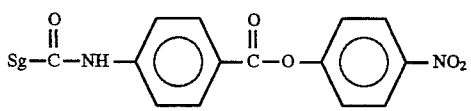 (30)

The N-SgCO-substituted-p-aminobenzoic acid prepared as an intermediate in the synthesis of 27 above is reacted with dicyclohexylcarbodiimide and p-nitrophenol to give the product.

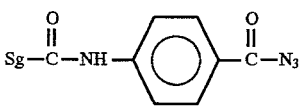 (31)

The compound shown as 27 above is reacted with sodium nitrite in aqueous acid to give the product. The product can also be obtained by reacting the N-SgCO-substituted-p-aminobenzoic acid prepared as an intermediate in the synthesis of 27 above with diphenylphosphorazidate.

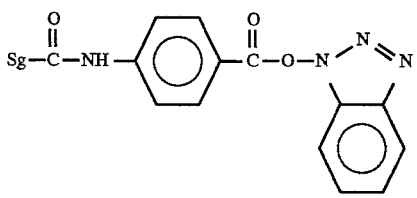 (32)

The N-SgCO-substituted-p-aminobenzoic acid prepared as an intermediate in the synthesis of 27 above is reacted with dicyclohexylcarbodiimide and N-hydroxybenzotriazole to give the product.

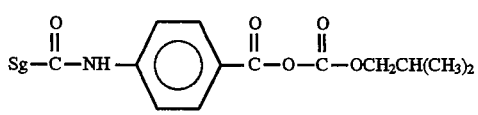 (33)

The N-SgCO-substituted-p-aminobenzoic acid prepared as an intermediate in the synthesis of 27 above is reacted with isobutylchloroformate to give the product.

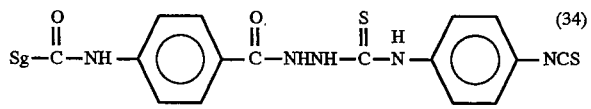 (34)

The compound shown as 27 is reacted with 1,4-phenylenediisothiocyanate (Aldrich) to give the product.

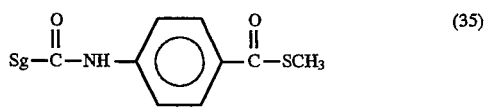 (35)

The compound shown as 29 is reacted with methanethiol (Aldrich) to give the product.

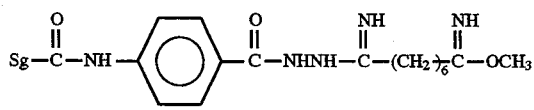 (36)

The compound shown as 27 is reacted with dimethylsuberimidate (Aldrich) to give the product.

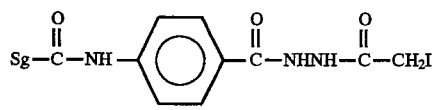 (37)

Iodoacetic acid is reacted with dicyclohexylcarbodiimide and N-hydroxysuccinimide to give iodoacetyl-N-hydroxysuccinimide, which is reacted in turn with compound 27 above to give the product.

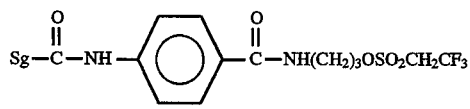 (38)

The N-hydroxysuccinimide ester of the N-SgCO-substituted-p-aminobenzoic acid prepared as an intermediate in the synthesis of 27 above is reacted with 3-aminopropanol (Aldrich) to give the corresponding 3-aminopropanol, which is reacted in turn with tresyl chloride to give the product.

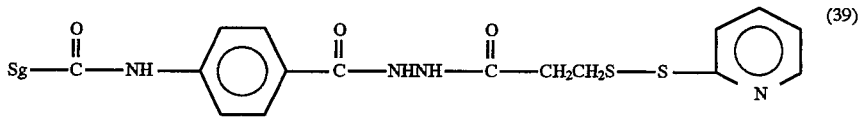

The compound shown as 27 is reacted with succinimidyl-3-(2-pyridyldithio) propionate (SPDP, Sigma) to give the product.

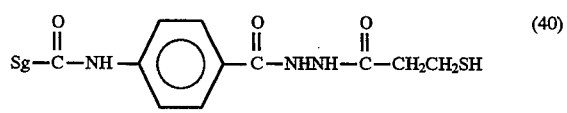 (40)

The compound shown as 39 above is reacted with dithiothreitol to give the product.

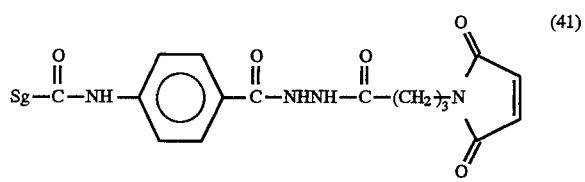 (41)

The compound shown as 27 is reacted with γ-maleimidobutyric acid N-hydroxysuccinimide to give the product.

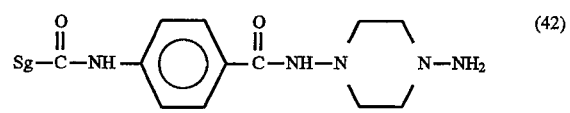 (42)

The N-hydroxysuccinimide ester of the N-SgCO-substituted-p-aminobenzoic acid prepared as an intermediate in the synthesis of 27 above is reacted with 1,4-diaminopiperazine to give this product.

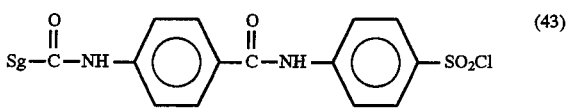 (43)

The N-hydroxysuccinimide ester of the N-SgCO-substituted-p-aminobenzoic acid prepared as an intermediate in the synthesis of 27 above is reacted with sulfanilic acid to give the corresponding sulfanilic acid derivative, which is reacted in turn with thionyl chloride to give the product.

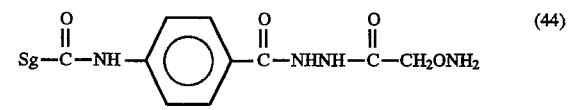 (44)

Carboxymethoxylamine is reacted with trifluoroacetic anhydride to give N-(trifluoroacetyl)carboxylamine. This latter compound is reacted with dicyclohexylcarbodiimide and the hydrazide shown as 27, followed by removal of the trifluoroacetyl groups at alkaline pH to give the product.

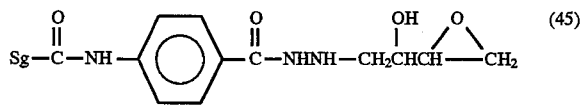 (45)

The compound shown as 27 is reacted with 1,2,3,4-diepoxybutane (Aldrich) to give the product.

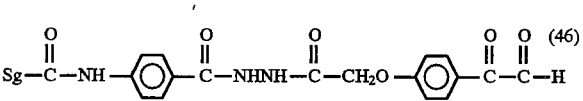 (46)

4-(Oxyacetyl)phenoxyacetic acid is prepared as described (Duerksen, P. J. and Wilkinson, K. D., Anal. Biochem. 160, 1987, pp. 444–454). This compound is then activated with dicyclohexylcarbodiimide and reacted with the compound shown as 27 to give the product.

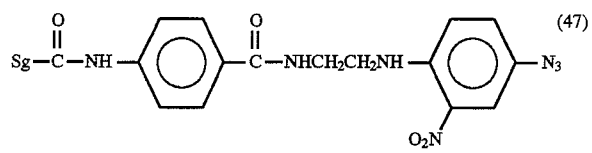

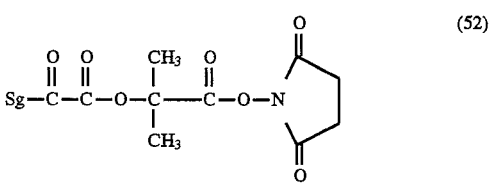

4-Fluoro-3-nitrophenyl azide is synthesized as described (Forster, A. C., McInnes, J. L., Skingle, D. C., and Symons, R. H., Nucl. Acids Res. 13, 1985, pp. 745–761) and reacted with the compound shown as 28 to form the product. Photolysis of the product as described (Forster, Ibid.) forms the corresponding release tag nitrophenyl nitrene.

An acid chloride of an electrophoric 2-oxo-carboxylic acid SgCOCO$_2$H (prepared as above in connection with compound 4) is reacted in the presence of pyridine with 2-hydroxyisobutyric acid, and the resulting substituted carboxylic acid is subsequently reacted with N,N'-carbonyldiimidazole and N-hydroxysuccinimide to give the product.

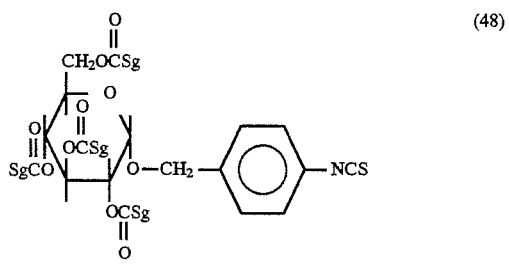

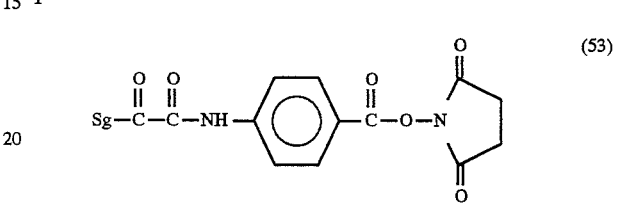

α-D-Glucopyranosylphenylisothiocyanate (Sigma) is reacted with an acid chloride of an electrophoric carboxylic acid SgCO$_2$H such as those shown in Table XIII in pyridine to give the product.

An acid chloride of an electrophoric 2-oxo-carboxylic acid SgCOCO$_2$H (prepared as above in connection with compound 4) is reacted with p-aminobenzoic acid, and the intermediate substituted carboxylic acid is then further reacted with N,N'-carbonyldiimidazole and N-hydroxysuccinimide to give the product.

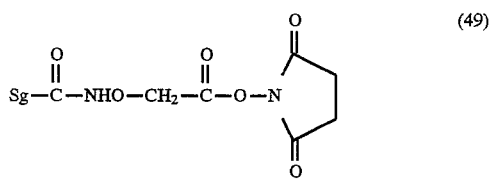

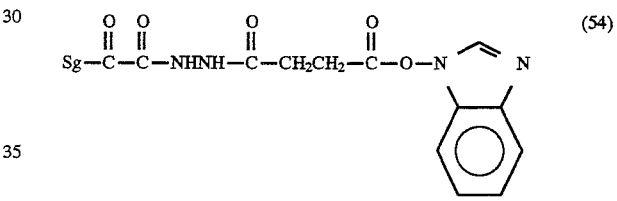

Carboxymethoxylamine hydrochloride (Aldrich) is reacted with the anhydride of an electrophoric carboxylic acid SgCO$_2$H such as those shown in Table XIII, followed by treatment of the initial product with N,N'-carbonyldiimidazole and N-hydroxysuccinimide to give the product.

An acid chloride of an electrophoric 2-oxo-carboxylic acid SgCOCO$_2$H (prepared as above in connection with compound 4) is reacted with hydrazine, and the resulting substituted hydrazine is further reacted with succinic anhydride and then with N,N'-dicyclohexylcarbodiimide and N-hydroxybenzotriazole to give the product.

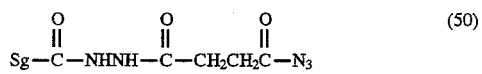

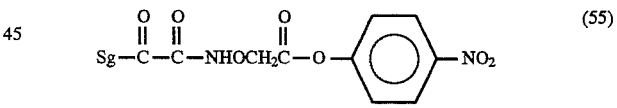

Hydrazine is reacted with the anhydride of an electrophoric carboxylic acid SgCO$_2$H such as those shown in Table XIII. The initially-formed product is then reacted successively with succinic anhydride, acidic methanol, and hydrazine, followed by NaNO$_2$ in aqueous acid to give the product.

An acid chloride of an electrophoric 2-oxo-carboxylic acid SgCOCO$_2$H (prepared as above in connection with compound 4) is reacted with carboxymethoxylamine, and the intermediate substituted carboxylic acid is further reacted with p-nitrophenol in the presence of N,N'-dicyclohexylcarbodiimide to give the product.

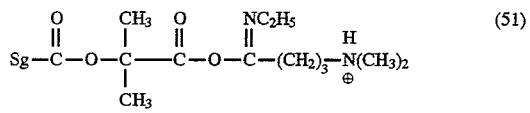

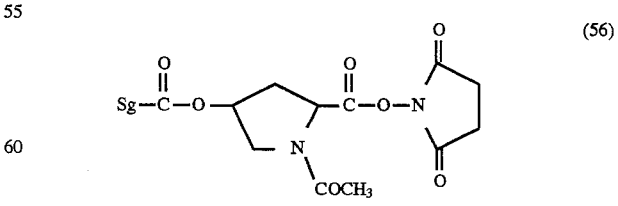

2-Hydroxyisobutyric acid (Aldrich) is reacted with the acid chloride of an electrophoric carboxylic acid SgCO$_2$H such as those shown in Table XIII, in the presence of pyridine, and the resulting substituted carboxylic acid is then reacted with the water-soluble carbodiimide 1-ethyl-3-(3-dimethylaminopropyl)-carbodiimide to give the product.

An acid chloride of an electrophoric carboxylic acid SgCO$_2$H such as those shown in Table XIII is reacted in the presence of pyridine with N-acetylhydroxyproline (Sigma), then the intermediate substituted carboxylic acid is further reacted with N,N'-dicyclohexylcarbodiimide and N-hydroxysuccinimide to give the product.

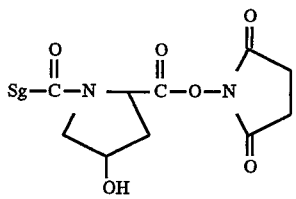
(57)

An anhydride of an electrophoric carboxylic acid SgCO$_2$H such as those shown in Table XIII is reacted with hydroxyproline (Sigma), and the intermediate substituted carboxylic acid is then further reacted with N,N'-dicyclohexylcarbodiimide and N-hydroxysuccinimide to give the product.

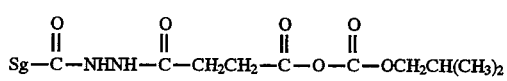
(58)

One equivalent of an anhydride of an electrophoric carboxylic acid SgCO$_2$H such as those shown in Table XIII is reacted with hydrazine, then the intermediate substituted hydrazine is further reacted with succinic anhydride, and the intermediate substituted carboxylic acid is finally reacted with isobutyl chloroformate to give the product.

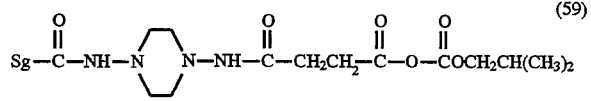
(59)

One equivalent of an anhydride of an electrophoric carboxylic acid SgCO$_2$H such as those shown in Table XIII is reacted with 1,4-diaminopiperazine, then the substituted aminopiperazine is further reacted with succinic anhydride, and finally the substituted carboxylic acid reacted with isobutyl chloroformate to give the product.

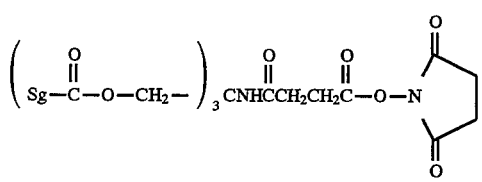
(60)

Tris-(hydroxymethyl)aminomethane (Aldrich) is reacted with succinic anhydride, the intermediate polyol is reacted with an acid chloride of an electrophoric carboxylic acid SgCO$_2$H such as those shown in Table XIII, and finally, the carboxylic acid is reacted with N,N'-dicyclohexylcarbodiimide and N-hydroxysuccinimide to give the product.

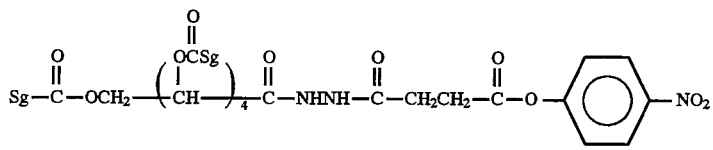
(61)

Gluconic acid lactone (Sigma) is reacted with hydrazine, the intermediate product is reacted with succinic anhydride, the hydroxyl functionalities are reacted in the presence of pyridine with an acid chloride of an electrophoric carboxylic acid SgCO$_2$H such as those shown in Table XIII, and finally, the substituted carboxylic acid is reacted with p-nitrophenol and N,N'-dicyclohexylcarbodiimide to produce the product.

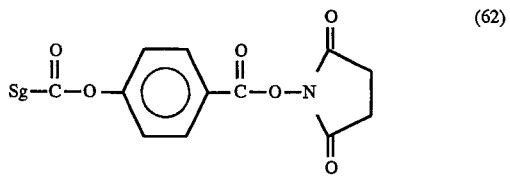
(62)

p-Hydroxybenzoic acid (Aldrich) is reacted in the presence of pyridine with an acid chloride of an electrophoric carboxylic acid SgCO$_2$H such as those shown in Table XIII, then the substituted carboxylic acid is further reacted with N,N'-dicyclohexylcarbodiimide and N-hydroxysuccinimide to give the product.

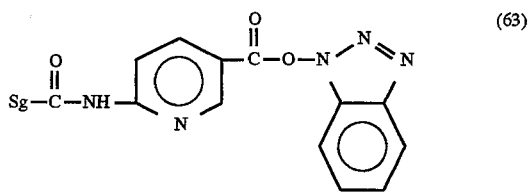
(63)

6-Aminonicotinic acid (Aldrich) is reacted with an anhydride of an electrophoric carboxylic acid SgCO$_2$H such as those shown in Table XIII, then the resulting substituted carboxylic acid is further reacted with N,N'-dicyclohexylcarbodiimide and N-hydroxybenzotriazole to yield the product.

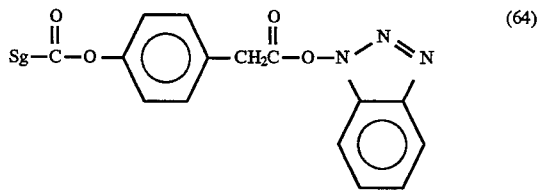
(64)

4-Hydroxyphenylacetic acid is reacted in the presence of pyridine with an acid chloride of an electrophoric carboxylic acid SgCO$_2$H such as those shown in Table XIII, then the intermediate substituted carboxylic acid is further reacted with N,N'-dicyclohexylcarbodiimide and N-hydroxybenzotriazole to yield the product.

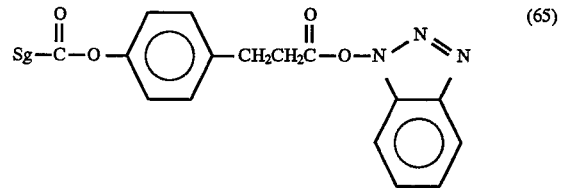
(65)

4-Hydroxyphenyl propionic acid (Aldrich) is treated as described above for the preparation of compound 64, to produce the product.

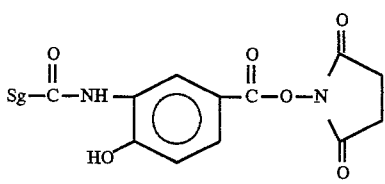
(66)

3-Amino-4-hydroxybenzoic acid (Aldrich) is reacted with an anhydride of an electrophoric carboxylic acid $SgCO_2H$ such as those shown in Table XIII, then the intermediate substituted carboxylic acid is further reacted with N,N'-carbonyldiimidazole and N-hydroxysuccinimide to give the product.

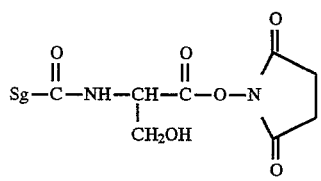
(67)

Serine (Sigma) is reacted with an anhydride of an electrophoric carboxylic acid $SgCO_2H$ such as those shown in Table XIII, then the intermediate substituted carboxylic acid is further reacted with N,N'-dicyclohexylcarbodiimide and N-hydroxysuccinimide to give the product.

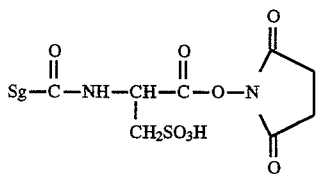
(68)

Cysteic acid (Sigma) is reacted as described above for the preparation of compound 67, to yield the product.

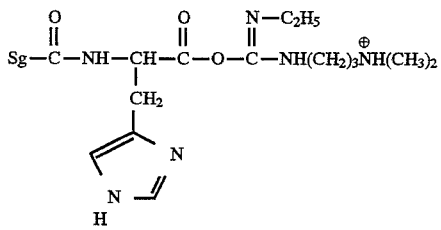
(69)

Histidine (Sigma) is reacted with an anhydride of an electrophoric carboxylic acid $SgCO_2H$ such as those shown in Table XIII, then the intermediate substituted carboxylic acid is further reacted with the water-soluble carbodiimide 1-ethyl-3-(3-dimethylaminopropyl)carbodiimide to give the product.

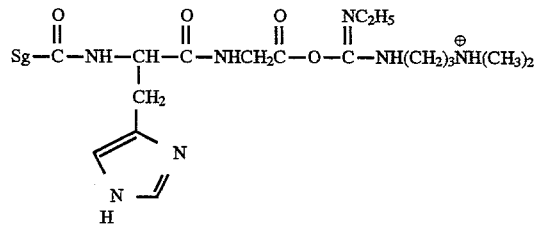
(70)

Histidylglycine (Sigma) is reacted with the reagents employed in the preparation of compound 69 above, to give the product.

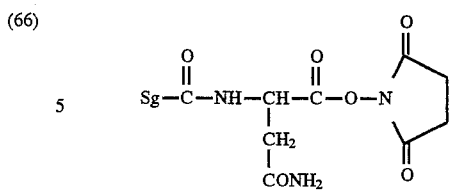
(71)

Asparagine (Sigma) is reacted with an anhydride of an electrophoric carbozylic acid $SgCO_2H$ such as those shown in Table XIII, and the intermediate substituted carboxylic acid is further reacted with N,N'-carbonyldiimidazole and N-hydroxysuccinimide to give the product. An analog may be made using glutamine instead of asparagine.

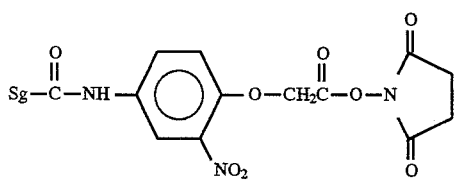
(72)

4-Amino-2-nitrophenol (Aldrich) is reacted with an anhydride of an electrophoric carboxylic acid $SgCO_2H$ such as those shown in Table XIII, the intermediate substituted phenol is further reacted with iodoacetate, then the substituted carboxylic acid is finally reacted with N,N'-dicyclohexylcarbodiimide and N-hydroxysuccinimide to give the product.

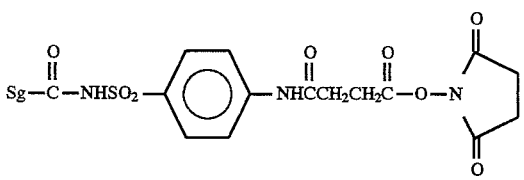
(73)

Sulfanilamide (Aldrich) is reacted with succinic anhydride, the intermediate carboxylic acid is then reacted at the sulfanilamide nitrogen with an acid chloride of an electrophoric carboxylic acid $SgCO_2H$ such as those shown in Table XIII, and the resulting substituted carboxylic acid is finally reacted with N,N'-dicyclohexylcarbodiimide and N-hydroxysuccinimide to give the product.

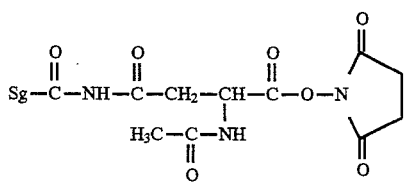
(74)

$N^\alpha$-acetylasparagine (Sigma) is reacted with an acid chloride of an electrophoric carboxylic acid $SgCO_2H$ such as those shown in Table XIII, then the substituted carboxylic acid is further reacted with N,N'-carbonyldiimidazole and N-hydroxysuccinimide to give the product. An analog may be made using $N^\alpha$-acetylglutamine instead of $N^\alpha$-acetylasparagine.

(75)
$$Sg-\overset{O}{\overset{\|}{C}}-NH-CH_2\overset{O}{\overset{\|}{C}}-NHCH_2\overset{O}{\overset{\|}{C}}-O-N\overset{O}{\underset{O}{\diagup}}$$

Glycylglycine (Sigma) is reacted with an anhydride of an electrophoric carboxylic acid $SgCO_2H$ such as those shown in Table XIII, then the intermediate substituted carboxylic acid is further reacted with N,N'-dicyclohexylcarbodiimide and N-hydroxysuccinimide to give the product.

(76)
$$Sg-\overset{O}{\overset{\|}{C}}-NH-\underset{N\diagdown_O}{\diagup}N-CH_2\overset{O}{\overset{\|}{C}}-O-N\overset{O}{\underset{O}{\diagup}}$$

Cytosine (Sigma) is reacted with an anhydride of an electrophoric carboxylic acid $SgCO_2H$ such as those shown in Table XIII, the resulting derivative is reacted with iodoacetate, and the substituted carboxylic acid produced in that reaction is further treated with N,N'-carbonyldiimidazole and N-hydroxysuccinimide to give the product.

(77)
$$Sg-\overset{O}{\overset{\|}{C}}-N\underset{OH}{\diagup}\overset{O}{\overset{\|}{C}}NHCH_2CH_2NH_2$$

The material shown as compound 57 above is reacted with ethylenediamine to give the product.

(78)
$$Sg-\overset{O}{\overset{\|}{C}}-NH-\underset{CH_2CONH_2}{CH}-\overset{O}{\overset{\|}{C}}-NHNH-\overset{S}{\overset{\|}{C}}-NH-\bigcirc-NCS$$

The compound shown as number 71 above is reacted with hydrazine and the resulting intermediate material is further reacted with 1,4-phenylenediisothiocyanate to give the product.

(79)
$$Sg-\overset{O}{\overset{\|}{C}}-\overset{O}{\overset{\|}{C}}-NHOCH_2CSCH_3$$

The material shown as compound 55 above is reacted with methane thiol (Aldrich) to give the product.

(80)
$$Sg-\overset{O}{\overset{\|}{C}}-NHNH-\overset{O}{\overset{\|}{C}}-CH_2CH_2-\overset{O}{\overset{\|}{C}}-NHNH-\overset{NH}{\overset{\|}{C}}+CH_2)_6\overset{NH}{\overset{\|}{C}}-OCH_3$$

The material shown as compound 58 above is reacted with hydrazine and the resulting product is further reacted with dimethylsuberimidate (Aldrich) to give the product.

(81)
$$Sg-\overset{O}{\overset{\|}{C}}-NHNH-\overset{O}{\overset{\|}{C}}-CH_2CH_2-\overset{O}{\overset{\|}{C}}-NH(CH_2)_3OSO_2CH_2CF_2$$

The material shown as compound 50 above is reacted with 3-aminopropanol (Aldrich) and the resulting alcohol is further reacted with tresyl chloride to give the product.

(82)
$$Sg-\overset{O}{\overset{\|}{C}}-NH-\underset{CH_2SO_3H}{CH}-\overset{O}{\overset{\|}{C}}-NHNH-\overset{O}{\overset{\|}{C}}-CH_2CH_2-S-S-\bigcirc_N$$

The material shown as compound 68 above is reacted with hydrazine, then the intermediate substituted hydrazine is further reacted with succinimidyl-3-(2-pyridyldithio)propionate (Sigma) to give the product.

(83)
$$Sg-\overset{O}{\overset{\|}{C}}-NH-\underset{CH_2SO_3H}{CH}-\overset{O}{\overset{\|}{C}}-NHNH-\overset{O}{\overset{\|}{C}}-CH_2CH_2SH$$

The material shown as compound 82 above is reacted with dithiothreitol to give the product.

(84)
$$Sg-\overset{O}{\overset{\|}{C}}-\overset{O}{\overset{\|}{C}}-NH-\bigcirc-\overset{O}{\overset{\|}{C}}-NH-\bigcirc-SO_2Cl$$

The material shown as compound 53 above is reacted with sulfanilic acid and the resulting intermediate product is further with thionyl chloride to give the product.

(85)
$$Sg-\overset{O}{\overset{\|}{C}}-NH-CH_2-\overset{O}{\overset{\|}{C}}-NH-CH_2-\overset{O}{\overset{\|}{C}}-NHNH-\overset{O}{\overset{\|}{C}}-CH_2ONH_2$$

Carboxymethoxylamine (Aldrich) is reacted with trifluoroacetic anhydride to give N-(trifluoroacetyl)carboxylamine. The material shown as compound 75 above is reacted with hydrazine, then with the N-(trifluoroacetyl)carboxylamine in the presence of the water-soluble carbodiimide 1-ethyl-3-(3-dimethylaminopropyl)carbodiimide followed by hydrolysis with aqueous sodium hydroxide to remove the trifluoroacetyl group and give the product.

(86)
$$Sg-\overset{O}{\overset{\|}{C}}-NH-\underset{CH_2OH}{CH}-\overset{O}{\overset{\|}{C}}-NHNHCH_2CH\overset{O}{\underset{}{\diagdown}}CH_2$$

The material shown as compound 67 above is reacted with hydrazine, then the resulting substituted hydrazine is further reacted with epibromohydrin (Aldrich) to give the product.

(87)
$$Sg-\overset{O}{\overset{\|}{C}}-NH-\bigcirc-\overset{O}{\overset{\|}{C}}-NHNH-\underset{O_2N}{\bigcirc}-N_3$$

4-Fluoro-3-nitrophenylazide is synthesized as described (Forster, Ibid.), and is then reacted with the material shown as compound 27 above to form the product. Subsequent photolysis as described (Forster, Ibid.) yields the corresponding nitrophenyl nitrene.

(88)
$$Sg-\overset{O}{\overset{\|}{C}}-NHNH-\overset{O}{\overset{\|}{C}}-CH_2CH_2-\overset{O}{\overset{\|}{C}}-O-N\overset{O}{\underset{O}{\diagup}}$$

One equivalent of an anhydride of an electrophoric carboxylic acid $SgCO_2H$ such as those shown in Table XIII is reacted with hydrazine, then the resulting substituted hydrazine is further reacted with succinic anhydride and the resulting substituted carboxylic acid is finally reacted with N,N'-dicyclohexylcarbodiimide and N-hydroxysuccinimide to give the product.

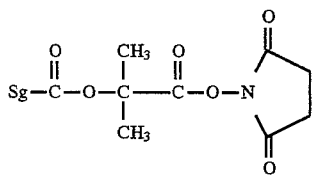
(89)

2-Hydroxyisobutyric acid (Aldrich) is reacted with an acid chloride of an electrophoric carboxylic acid $SgCO_2H$ such as those shown in Table XIII, then the resulting substituted carboxylic acid is further reacted with N,N'-dicyclohexylcarbodiimide and N-hydroxysuccinimide to give the product.

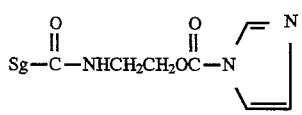
(90)

The anhydride of an electrophoric carboxylic acid $SgCO_2H$ such as those shown in Table XIII is reacted with ethanolamine and the resulting substituted alcohol is further reacted with N,N'-carbonyldiimidazole to give the product.

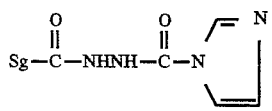
(91)

The anhydride of an electrophoric carboxylic acid $SgCO_2H$ such as those shown in Table XIII is reacted with hydrazine and the resulting substituted hydrazine is further reacted with N,N'-carbonyldiimidazole to give the product.

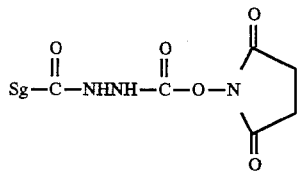
(92)

The anhydride of an electrophoric carboxylic acid $SGCO_2H$ such as those shown in Table XIII is reacted with hydrazine, and the resulting substituted hydrazine is further reacted with disuccinimidyl carbonate to give the product.

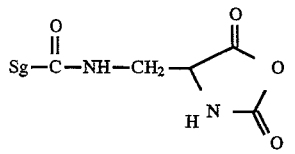
(93)

2,3-Diaminopropionic acid (Aldrich) is reacted with one equivalent of an anhydride of an electrophoric carboxylic acid $SgCO_2H$ such as those shown in Table XIII, yielding a mixture of N2-SgCO-2,3-diaminopropionic acid and N3-SgCO-2,3-diaminopropionic acid. The latter compound is isolated and reacted with phosgene to give the product.

(94)

An anhydride of an electrophoric carboxylic acid $SgCO_2H$ such as those shown in Table XIII is reacted with carbohydrazide to give the product.

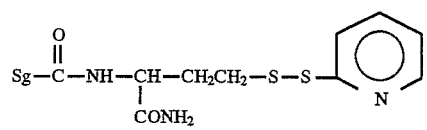
(95)

Homocysteine thiolactone is reacted with an anhydride of an electrophoric carboxylic acid $SgCO_2H$ such as those shown in Table XIII, the resulting carboxylic acid is further reacted with ammonia, and the resulting thiol-containing amide is finally reacted with 2,2'-dipyridyldisulfide to give the product.

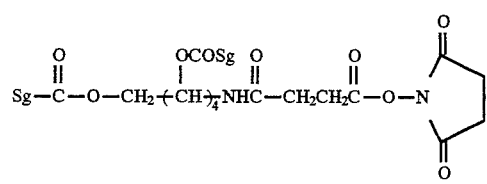
(96)

Glucosamine (Sigma) is reacted with sodium borohydride and the resulting intermediate product is further reacted with succinic anhydride. The substituted carboxylic acid resulting from this reaction is reacted in turn, in the presence of pyridine, with an acid chloride of an electrophoric carboxylic acid $SgCO_2H$ such as those shown in Table XIII, and then with N,N'-dicyclohexylcarbodiimide and N-hydroxysuccinimide to give the desired product.

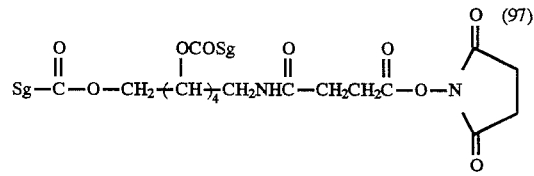
(97)

Glucose (Sigma) is reacted with ammonia and sodium borohydride and the resulting amine is then reacted with succinic anhydride to form a substituted cayboxylic acid. This is reacted in turn, in the presence of pyridine, with an acid chloride of an electrophoric carboxylic acid $SgCO_2H$ such as those shown in Table XIII, and then further reacted with N,N'-dicyclohexylcarbodiimide and N-hydroxysuccinimide to give the product. For this reaction glucamine can also be obtained from Hiils America.

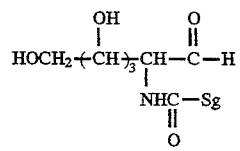
98)

Glucosamine (Sigma) is reacted with an anhydride of an electrophoric carboxylic acid $SgCO_2H$ such as those shown in Table XIII to give the product.

(SgCO)$_x$Dextran hydrazide (99)

Dextran hydrazide is partly reacted with an anhydride of an electrophoric carboxylic acid $SgCO_2H$ such as those shown in Table XIII to give the product.

(SgCO)ₓDextran hydrazide-succinyl-EDAC (100)

The material shown as compound 99 above is reacted with succinic anhydride and the resulting succinyl derivative is further reacted with the water-soluble carbodiimide 1-ethyl-3-(3-dimethylaminopropyl)carbodiimide to give the product.

(SgCO)ₓDextran-carbonyl imidazole (101)

Dextran is reacted in the presence of pyridine with an acid chloride of an electrophoric carboxylic acid SgCO₂H such as those shown in Table XIII, then the resulting dextran derivative is further reacted with N,N'-carbonyldiimidazole to give the product.

(SgCO)ₓDextran aldehyde (102)

Dextran is reacted in the presence of pyridine with an acid chloride of an electrophoric carboxylic acid SgCO₂H such as those shown in Table XIII, then the resulting dextran derivative is treated with aqueous periodate to give the product.

(SgCO)ₓPoly(ser)-EDAC (103)

Poly(ser) is reacted in the presence of pyridine with an acid chloride of an electrophoric carboxylic acid SgCO₂H such as those shown in Table XIII, then the intermediate polymer derivative is further reacted with the water-soluble carbodiimide 1-ethyl-3-(3-dimethylamino- propyl)carbodiimide to give the product.

Nᵅ-acetyl-(SgCO)ₓPoly(ser)-DAO-succinyl-EDAC (104)

Poly(ser) is reacted with acetic anhydride followed by reaction in the presence of pyridine with an acid chloride of an electrophoric carboxylic acid SgCO₂H such as those shown in Table XIII. The resulting polymer derivative is then treated with 1-ethyl-3-(3-dimethylaminopropyl) carbodiimide (EDAC) and 1,8-diaminooctane. The resulting product is further treated with succinic anhydride followed by EDAC to give the product.

(SgCO)ₓPoly(C)-hydrazide (105)

Poly(C)-hydrazide is partly reacted with an anhydride of an electrophoric carboxylic acid SgCO₂H such as those shown in Table XIII to give the product.

(SgCO)ₓPoly(C)-hydrazide-succinyl-EDAC (106)

The material shown as compound 105 above is reacted further with acetic anhydride and then with 1-ethyl-3-(3-dimethylaminopropyl)carbodiimide to give the product.

(SgCO)ₓpoly(gly)-EDAC (107)

Poly(gly) is reacted in the presence of pyridine with an acid chloride of an electrophoric carboxylic acid SgCO₂H such as those shown in Table XIII, then further reacted with 1-ethyl-3-(3-dimethylaminopropyl)carbodiimide to give the product.

Nᵅ-Acetyl-(SgCO)ₓPoly(gly)-DAO (108)

Poly(gly) is reacted first with acetic anhydride and then further reacted in the presence of pyridine with an acid chloride of an electrophoric carboxylic acid SgCO₂H such as those shown in Table XIII, and finally reacted further with 1-ethyl-3-(3-dimethylaminopropyl)carbodiimide and 1,8-diaminooctane to give the product.

(SgCO)ₓPoly(asp)-hydrazide (109)

Poly(asp)-hydrazide is partly reacted with an anhydride of an electrophoric carboxylic acid SgCO₂H such as those shown in Table XIII, to give the product.

(SgCO)ₓPoly(asp)-hydrazide-succinyl-EDAC (110)

The material shown as compound 109 above is further reacted with succinic anhydride and then with 1-ethyl-3-(3-dimethylaminopropyl)carbodiimide (EDAC), to give the product.

(SgCO)ₓGlycol chitosan (111)

Glycol chitosan is partially reacted with the anhydride of an electrophoric carboxylic acid SgCO₂H such as those shown in Table XIII, to give the product.

(SgCO)ₓGlycol chitosan-succinyl-EDAC (112)

The material identified as compound 111 above is further reacted with succinic anhydride and then with 1-ethyl-3-(3-dimethylaminopropyl)carbodiimide (EDAC), to give the product.

(SgCO)ₓPoly(acrylamide)-ED-succinyl-EDAC (113)

Poly(acrylamide)-ED is partly reacted with an anhydride of an electrophoric carboxylic acid SgCO₂H such as those shown in Table XIII, and then further reacted with 1-ethyl-3-(3-dimethylaminopropyl)carbodiimide (EDAC), to give the product.

(SgCO)ₓPoly(asn)-EDAC (114)

Poly(asn) is reacted in the presence of pyridine with an acid chloride of an electrophoric carboxylic acid SgCO₂H such as those shown in Table XIII, then the product of this reaction is further treated with 1-ethyl-3-(3-dimethylaminopropyl)carbodiimide (EDAC), to give the product.

(SgCO)ₓPoly(asn)-DAO (115)

Poly(asn) is reacted in the presence of pyridine with an acid chloride of an electrophoric carboxylic acid SgCO₂H such as those shown in Table XIII, and then reacted further with 1-ethyl-3-(3-dimethylaminopropyl)carbodiimide (EDAC) and 1,8-diaminooctane (DAO), to give the product.

(SgCO$_s$Poly(asn)-DAO-succinyl-EDAC (116)

The material shown as compound 115 above is reacted further with succinic anhydride and then finally with 1-ethyl-3-(3-dimethylaminopropyl)carbodiimide (EDAC) to give the product.

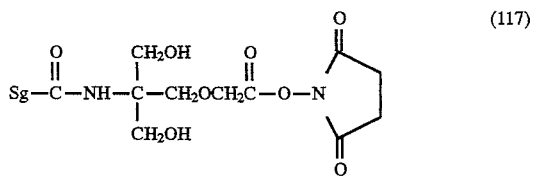
(117)

Tris-(hydroxymethyl)aminomethane (Sigma) is reacted with an anhydride of an electrophoric carboxylic acid $SgCO_2H$ such as those shown in Table XIII, and then treated with a solution of barium hydroxide. The product of this reaction is further treated with methylchloroacetate and sodium hydride, then treated with aqueous sodium hydroxide, and finally reacted with N,N'-dicyclohexylcarbodiimide and N-hydroxysuccinimide to give the product.

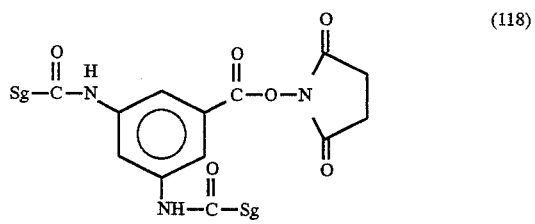
(118)

3,5-Diaminobenzoic acid (Aldrich) is reacted with the anhydride of an electrophoric carboxylic acid $SgCO_2H$ such as those shown in Table XIII, and the resulting material is further reacted with N,N'-dicyclohexylcarbodiimide and N-hydroxysuccinimide to give the product.

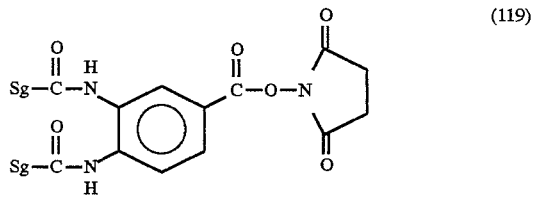
(119)

This material is prepared in the same way as compound 118 above except that 3,4-diaminobenzoic acid (Aldrich) is employed as a starting material.

A release tag-labeled antibody is prepared by reacting an antibody with a release tag reagent having a reactive functional group capable of covalently attaching to the antibody. Examples of release tags which are suitable for conjugation with an antibody are: $CCl_3CO$-AB-NHS, $CCl_3CO$-MAB-NHS, $CCl_2CClCO$-AB-NHS, $CCl_3$-diol-gly-NHS, and SgCO-CHOH-NHS, where AB stands for p-aminobenzoic acid, MAB stands for N-methyl-p-aminobenzoic acid, and NHS stands for N-hydroxysuccinimide. Also included among the exemplary release tags are the compounds, numbered as 46, 48–76, 78–80, 86–93, 96, 97, 100, 101, 103, 104, 106, 107, 110, 112, 113, 114, 116, and 117, where the numbers refer to the release tags shown in the above listing of exemplary release tag compounds. This grouping of release tag compounds which are suitable for labeling antibodies is referred to as Group I in the discussion below.

A release tag-labeled antibody can also be prepared by reacting an antibody in the presence of 1-ethyl-3-(3-dimethylaminopropyl)carbodiimide (EDAC) with one of the following release tags: 27, 77, 85, 94, 99, 105, 108, 109, 111, and 115, where these numbers refer to the above-listed exemplary release tag compounds. The above-identified set of release tag compounds which are suitable for the reaction with an antibody in the presence of EDAC are defined as Group II for purposes of the discussion to follow. In addition, a release tag-labeled antibody can be prepared by reacting an antibody with exemplary release tag compounds 98 or 102, defined as Group III, in the presence of $NaCNBH_3$ or $NaBH_4$.

A release tag-labeled antibody can also be prepared by reacting the antibody with aqueous periodate and then with a release tag from Group II in the presence of $NaCNBH_3$ or $NaBH_4$.

A release tag-labeled DNA can be prepared by preparing an aminoalkyl DNA as described (Ehrat, M., Cecchini, D. and Giese, R. W., J. Chromatogr. 326, 1985, pp. 311–320) and subsequently reacting this with a release tag from Groups I, II, or III as defined above.

A release tag-labeled DNA can also be prepared by reacting the DNA in the presence of $NaHSO_3$ as described (Ehrat, Ibid.) with a release tag from Group II.

A release tag-labeled avidin, streptavidin, protein A, protein G, or lectin can be prepared by reacting it as above with a release tag compound from Group I.

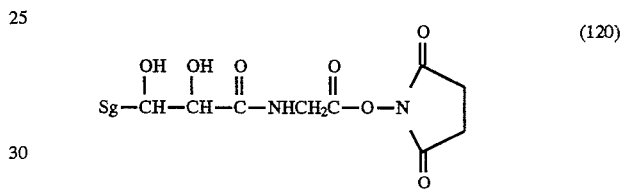
(120)

An α,β-unsaturated carboxylic acid bearing a β-Sg substituent is prepared in any of the ways known to the art, then the double bond is oxidized to the diol by reaction with osmium tetroxide in the presence of pyridine and THF. This oxidation can also be accomplished by reacting the olefinic carboxylic acid with performic acid as described by Wagner and Zook, Synthetic Organic Chemistry, Wiley Interscience, N.Y., pp. 179–180, 1953. The α,β-dihydroxy carboxylic acid is then reacted with glycine methyl ester in the presence of N,N'-dicyclohexylcarbodiimide, the ester functionality is saponified by treatment with base, and finally, the resulting carboxylate is reacted with N-hydroxysuccinimide in the presence of DCC to yield the desired product. For the particular case in which the group Sg is $Cl_3$—, the starting Sg-substituted α,β-unsaturated carboxylic acid can be produced from 3-hydroxy-4,4,4-trichlorobutyric-β-lactone (Aldrich) by acid hydrolysis to effect dehydration as described by Wagner and Zook, Ibid., p. 50. Alternatively, one can start with this same lactone, and brominate it to yield the α-bromolactone as described by House in "Modern Synthetic Reactions" 2nd Ed., W. A. Benjamin, Menlo Park, Calif., pp. 476–478 or 459 and 473, 1972. Upon hydrolysis as described by Wagner and Zook, Ibid., pp. 170–171, the α,β-dihydroxy carboxylic acid is produced, and this is in turn reacted further with glycine methyl ester and N-hydroxysuccinimide to produce the product as described above.

Sg-diol-CO-gly-BSA (121)

BSA is reacted with the material shown above as compound 120 to form the product. Upon oxidation with aqueous permanganate-periodate as described by House, Ibid., p. 278, the diol is cleaved and SgH is released.

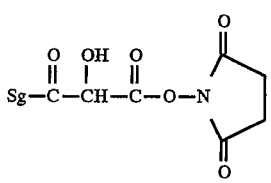

(122)

This α-hydroxy ketone is prepared by any of the following three procedures:

(a) Acetic acid is reacted with two equivalents of NaH, the product is treated with an anhydride of an electrophoric carboxylic acid SgCO₂H such as those shown in Table XIII, the product of this step is further treated with bromine and sodium carbonate, then treated with sodium hydroxide, reacidified, and finally subjected to N-hydroxysuccinimide in the presence of N,N'-dicyclohexylcarbodiimide to give the desired product.

(b) The acid chloride of an electrophoric carboxylic acid SgCO₂H such as those shown above in Table XIII is reacted with methanol to give SgCO₂CH₃. Methyl acetate is reacted with sodium methoxide and the resulting carbanion is reacted with the SgCO₂CH₃ to yield SgCOCH₂CO₂CH₃. This is brominated in the presence of sodium bicarbonate, the product is saponified, then reacidified, and finally, the resulting acid is treated with N-hydroxysuccinimide in the presence of N,N'-dicyclohexylcarbodiimide to yield the product.

(c) Sg-CO-CHO is reacted with HCN, the mixture is acidified, and the resulting carboxylic acid is treated with N-hydroxysuccinimide in the presence of N,N'-dicyclohexylcarbodiimide to give the product.

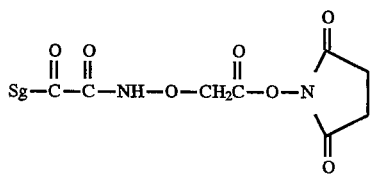

(123)

The material shown above as compound 7 is reacted with dicyclohexylcarbodiimide and N-hydroxysuccinimide to give the product.

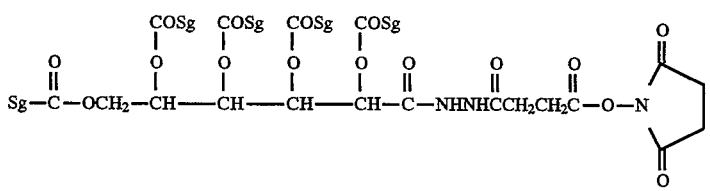

(124)

The material shown above as compound 13 is reacted with dicyclohexylcarbodiimide and N-hydroxysuccinimide to give the product.

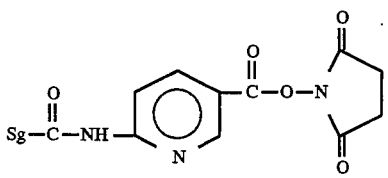

(125)

The material shown above as compound 15 is reacted with dicyclohexylcarbodiimide and N-hydroxysuccinimide to give the product.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A release tag compound for labeling substances for analytical purposes, said compound being represented by the formula Sg—CO—L—Rx wherein:

each Sg is a signal group, each CO is a carbonyl group to which an Sg is bonded, each Rx is a reactivity group, L is a linking group to which each SgCO group and each Rx group are bonded, and each COL portion is a release group which is cleavable to release an Sg-containing compound; and wherein:

each Sg is a C-linked organic moiety containing from 1 to 20 carbon atoms, the carbon atom of Sg which is bonded to the carbonyl carbon adjacent to linking group L being denominated as the α-position, and Sg comprises a radical selected from the group consisting of substituted alkyl, substituted keto-alkyl, substituted alkenyl, and substituted alkynyl radicals; said substituted alkyl, substituted keto-alkyl, and substituted alkenyl radicals bearing at least two electronegative substituents, and said substituted alkynyl radicals bearing at least one electronegative substituent; said electronegative substituents being selected from the group consisting of halogens, cyano, dihalomethyl and trihalomethyl; and further, 1) when Sg is keto-alkyl, alkenyl, or alkynyl, Sg comprises at least one moiety selected from the group consisting of:

β-E-alkynyl, α-E-α-alkynyl, β-E-α-keto (provided that the carbonyl carbon adjacent to linking group L is connected to a nitrogen or oxygen atom of L), α-E-alkenyl, and α-E-α-alkenyl, wherein E is an electronegative substituent selected from the group consisting of halogens, cyano, dihalomethyl, and trihalomethyl;

2) when Sg is alkyl, the α-carbon atom bears at least two of said electronegative substituents but no more than one fluorine atom;

each Sg being further selected such that upon cleavage of said release tag compound at said COL portion, signal group Sg is released in a volatile form suitable for electron capture determination in the gas phase;

L is oxy or amino; and

Rx comprises a phenylene moiety which is connected to L and which contains a reactive, functional group.

2. The compound of claim 1 wherein Sg is selected from a group consisting of CHCl₂—, CHBr₂—, CCl₃—, CBr₃—, and Cl₂C=CCl—.

3. The compound of claim 1 wherein Sg is selected from a group consisting of CBrCl₂—, CCl₂I—, CBr₂I—, $CBr_2F$—, $CCl_2F$—, $CBr_2Cl$—, $CH_3CBr_2$—, $CH_3CCl_2$—, $CCl_3CCl_2$—, and $CCl_3CBrCl$—.

4. The compound of claim 1 wherein Sg is selected from a group consisting of $CBrCl_2CBrCl$—, $CCl_3CBr_2$—, $CBr_2ClCCl_2$—, $CBr_3CCl_2$—, $CBr_2ClCBrCl$—, $CBrCl_2CBr_2$—, $CBr_3CBrCl$—, $CBr_2ClCBr_2$—, $CBr_3CBr_2$—, and $CHCl_2CCl_2$—.

5. The compound of claim 1 wherein Sg is selected from a group consisting of $CCl_3CHCl$—, $CHCl_2CBrCl$—, $CBrCl_2CHCl$—, $CCl_3CHBr$—, $CHBrClCCl_2$—, $CHBrClCBrCl$—, $CHBr_2CCl_2$—, $CHCl_2CBr_2$—, $CBr_3CHCl$—, and $CBr_2ClCHBr$—.

6. The compound of claim 1 wherein Sg is selected from a group consisting of $CHBr_2CBrCl$—, $CHBrClCBr_2$—, $CHBr_2CBr_2$—, $CBr_3CHBr$—, $CBrCl_2CCl_2$—, $CH_2BrCCl_2$—, $CHBrClCHCl$—, $CH_2ClCBrCl$—, $CHCl_2CHBr$—, and $CHBr_2CHCl$—.

7. The compound of claim 1 wherein Sg is selected from a group consisting of $C_6H_5CBr_2$—, $CHBrClCHBr$—, $CH_2ClCBr_2$—, $C_6H_5CCl_2$—, $CHBr_2CHBr$—, $CH_2BrCBr_2$—, $CH_2ClCCl_2$—, $CHCl_2CHCl$—, and $C_{10}H_7CCl_2$—.

8. The compound of claim 1 wherein Sg is selected from a group consisting of $CCl_3CClI$—, $CCl_2ICCl_2$—, $CClF_2CClF$—, $CBrF_2CBrF$—, $CF_2ICClF$—, $CClF_2CFI$—, $C_{10}H_7CBr_2$—, $CCl_2FCCl_2$—, $CCl_2FCHCl$—, and $CCl_2FCHF$—.

9. The compound of claim 1 wherein Sg is selected from a group consisting of $CF_3CCl_2$—, $CF_3CHCl$—, $CF_3CBr_2$—, $CCl_2FCBr_2$—, $CBr_2FCBr_2$—, $CBr_2FCHF$—, $CBr_2FCCl(CN)$—, $N{\equiv}CCCl_2$—, $N{\equiv}CCBr_2$—, and $N{\equiv}CCH_2CCl_2$—.

10. The compound of claim 1 wherein Sg is selected from a group consisting of $N{\equiv}CCH_2CBr_2$—, $CCl_3CCl(CN)$—, $CCl_3CBr(CN)$—, $CCl_3CF(CN)$—, $CBr_3CCl(CN)$—, $CHBr{=}CBr$—, $CHCl{=}CCl$—, $Br_2C{=}CBr$—, $BrClC{=}CCl$—, and $BrClC{=}CBr$—.

11. The compound of claim 1 wherein Sg is selected from a group consisting of

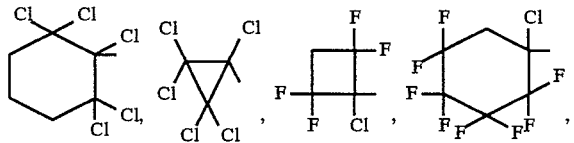

$ClC{\equiv}C$—, $HC{\equiv}CCHCl$—, $CF_3CCl_2CO$—, $N{\equiv}CCCl_2CO$—, and $HBrC{=}CBrCHCl$—.

* * * * *

UNITED STATES PATENT AND TRADEMARK OFFICE
CERTIFICATE OF CORRECTION

PATENT NO. : 5,650,270
DATED : July 22, 1997
INVENTOR(S) : Roger W. Giese, et al.

It is certified that error appears in the above-identified patent and that said Letters Patent is hereby corrected as shown below:

In the Abstract, line 6, "$(SgCo)_xL(Rx)_r$" should read --$(SgCO)_sL(RX)_r$--.

Column 2, line 24, "Tray., 35," should read --Trav., 35,--.

Column 5, line 30, "$CCl_2|CClH$" should read --$CCl_2=CClH$--.

Column 8, line 3, "contain at preferred" should read --contain at least three electronegative substituents. Particularly preferred--.

Column 8, line 4, "Particularly two or three" should read --two or three--.

Column 18, line 64, "such that widen each" should read --such that when each--.

Column 19, line 15, "chemical bend" should read --chemical bond--.

Column 24, line 47, "hereto atom" should read --hetero atom--.

Column 23, Table X, vertical line #'s 1-18 (first column) should be deleted. These numbers are not part of the Table X, but were simply line numbering on the pages of the specification as filed.

UNITED STATES PATENT AND TRADEMARK OFFICE
CERTIFICATE OF CORRECTION

PATENT NO. : 5,650,270
DATED : July 22, 1997
INVENTOR(S) : Roger W. Giese, et al.

It is certified that error appears in the above-identified patent and that said Letters Patent is hereby corrected as shown below:

Column 24, line 47, "hereto atom" should read --hetero atom--.

Column 25, Table XII, vertical line #'s 4-11 (first column) should be deleted. These numbers are not part of the Table XII, but were simply line numbering on the pages of the specification as filed.

Column 25, line 56, "aloe" should read --are--.

Column 26, line 19, "monophosghate" should read --monophosphate--.

Column 28, line 8, "suck as" should read --such as--.

Column 35, line 50, "the" should read --The--.

Column 42, line 25, "carbexylic" should read --carboxylic--.

UNITED STATES PATENT AND TRADEMARK OFFICE
CERTIFICATE OF CORRECTION

PATENT NO. : 5,650,270
DATED : July 22, 1997
INVENTOR(S) : Roger W. Giese, et al.

It is certified that error appears in the above-identified patent and that said Letters Patent is hereby corrected as shown below:

Column 45, equation 21, " 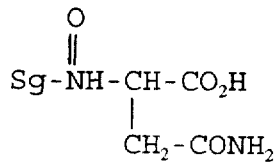 "

should read -- 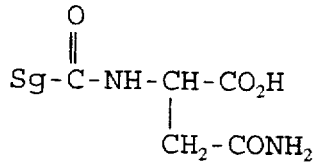 --.

Column 65, line 8, "CHCl$_2$CBrCi-" should read --CHCl$_2$CBrCl---.

Signed and Sealed this

Fifteenth Day of September, 1998

Attest:

*Attesting Officer*

BRUCE LEHMAN
*Commissioner of Patents and Trademarks*